(12) United States Patent
Matsushita et al.

US008722861B2

(10) Patent No.: US 8,722,861 B2
(45) Date of Patent: May 13, 2014

(54) MONOCLONAL ANTIBODIES THAT BIND TO THE V3 LOOP OF HIV-1 GP120

(75) Inventors: Shuzo Matsushita, Kumamoto (JP); Kazuhisa Yoshimura, Kumamoto (JP)

(73) Assignee: Kumamoto University, Kumamoto (JP)

( * ) Notice: Subject to any disclaimer, the term of this patent is extended or adjusted under 35 U.S.C. 154(b) by 581 days.

(21) Appl. No.: 12/743,442

(22) PCT Filed: Nov. 19, 2008

(86) PCT No.: PCT/JP2008/071035
§ 371 (c)(1), (2), (4) Date: Oct. 14, 2010

(87) PCT Pub. No.: WO2009/066702
PCT Pub. Date: May 28, 2009

(65) Prior Publication Data
US 2011/0044995 A1      Feb. 24, 2011

(30) Foreign Application Priority Data

Nov. 19, 2007 (JP) ................................. 2007-299083

(51) Int. Cl.
*C07K 16/00* (2006.01)
*A61K 39/42* (2006.01)

(52) U.S. Cl.
USPC .................................. 530/388.35; 424/160.1

(58) Field of Classification Search
None
See application file for complete search history.

(56) References Cited

U.S. PATENT DOCUMENTS 5,712,373 A    1/1998  Eda et al.
5,922,325 A    7/1999  Tilley et al.

FOREIGN PATENT DOCUMENTS

JP      04-152893    5/1992
JP      06-502539    3/1994
WO      92/07878     5/1992
WO      93/19786     10/1993

OTHER PUBLICATIONS

Winkler, K., et al., 2000, Changing the antigen binding specificity by single point mutations of an anti-p24 (HIV-1) antibody, J. Immunol. 165:4505-4514.*
Fanning, L. J., et al., 1996, Development of the immunoglobulin repertoire, Clin. Immunol. Immunopath. 79(1):1-14.*
Montefiori, D. C., Jun. 2005, Neutralizing antibodies take a swipe at HIV in vivo, Nat. Med. 11(6):593-594.*
Letvin, N. L., Dec. 2006, Progress and obstacles in the development of an AIDS vaccine, Nature 6:930-939.*
Burton et al., "HIV Vaccine Design and the Neutralizing Antibody Problem" *Nat. Immunol.*, vol. 5, No. 3, pp. 233-236 (2004).
Zolla-Pazner, "Identifying Epitopes of HIV-1 that Induce Protective Antibodies," *Nat. Rev. Immunol.*, vol. 4, No. 3, pp. 199-210 (2004).
Eda et al., "Sequential Immunization with V3 Peptides from Primary Human Immunodeficiency Virus Type I Produces Cross-Neutralizing Antibodies against Primary Isolates with a Matching Narrow-Neutralization Sequence Motif" *J. Virol.*, vol. 80, No. 11, pp. 5552-5562 (2006).
Haynes et al., "Cardiolipin Polyspecific Autoreactivity in Two Broadly Neutralizing HIV-1 Antibodies," *Science*, vol. 308, No. 5730, pp. 1906-1908 (2005).
Li et al., "Human Immunodeficiency Virus Type 1 env Clones from Acute and Early Subtype B Infections for Standardized Assessments of Vaccine-Elicited Neutralizing Antibodies" *J. Virol.*, vol. 79, No. 16, pp. 10108-10125 (2005).
International Search Report for PCT/JP2008/071035, mailed Feb. 24, 2009.
Yamaguchi et al., "Human Monoclonal Antibody with Dual GM2/GD2 Specificity Derived from an Immunized Melanoma Patient," *Proc. Natl. Acad. Sci. USA*, vol. 87, pp. 3333-3337, 1990.
Matsushita et al., "Human Monoclonal Antibody Directed Against an Envelope Glycoprotein of Human T-Cell Leukemia Virus Type I," *Proc. Natl. Acad. Sci. USA*, vol. 83, pp. 2672-2676, 1986.
Moore et al., "Probing the Structure of the V2 Domain of Human Immunodeficiency Virus Type 1 Surface Glycoprotein gp120 with a Panel of Eight Monoclonal Antibodies: Human Immune Response to the V1 and V2 Domains," *J. Virol.*, vol. 67, No. 10, pp. 6136-6151, 1993.
Saphire et al., "Crystal Structure of a Neutralizing Human IgG Against HIV-1: A Template for Vaccine Design," *Science*, vol. 293, pp. 1155-1159, 2001.
Marks et al., "By-passing Immunization: Human Antibodies from V-gene Libraries Displayed on Phage," *J. Mol. Biol.*, vol. 222, No. 3, pp. 581-597, 1991.
Wu et al., "Rational Design of Envelope Identifies Broadly Neutralizing Human Monoclonal Antibodies to HIV-1," *Science*, vol. 329, pp. 856-861, 2010.
International Preliminary Report on Patentability for PCT/JP2008/071035, mailed Jun. 3, 2010.
Supplementary European Search Report issued with respect to European Patent Application No. 08852125.7, dated May 31, 2012.

(Continued)

*Primary Examiner* — Jeffrey Parkin
(74) *Attorney, Agent, or Firm* — Greenblum & Bernstein, P.L.C.

(57) ABSTRACT

The present invention provides a monoclonal antibody that recognizes the V3 loop of the envelope glycoprotein gp120 of AIDS virus, which is any one selected from the following antibodies:

(a) an antibody having the amino acid sequence shown in SEQ ID NO: 1 as the amino acid sequence of a H chain variable region (VH), and having the amino acid sequence shown in SEQ ID NO: 2 as the amino acid sequence of a L chain variable region (VL); and (b) an antibody having the amino acid sequence shown in SEQ ID NO: 3 as the amino acid sequence of a H chain variable region (VH), and having the amino acid sequence shown in SEQ ID NO: 4 as the amino acid sequence of a L chain variable region (VL).

7 Claims, 15 Drawing Sheets

(56) References Cited

OTHER PUBLICATIONS

Laal et al., "Synergistic neutralization of human immunodeficiency virus type 1 by combinations of human monoclonal antibodies", *Journal of Virology*, vol. 68, No. 6, pp. 4001-4008, 1994.
Chinese Office Action issued with respect to patent family member Chinese Patent App. No. 200880125590.3 issued Oct. 10, 2012, along with an English-language translation.
McKeating et al., "Synergistic Interaction between Ligands Binding to the CD4 Binding Site and V3 Domain of Human Immunodeficiency Virus Type I gp120" *Virology* 191:732-42, 1992.
European Office Action issued with respect to patent family member European Patent Application No. 08 852 125.7, dated Feb. 7, 2013.
Chinese Office Action issued with respect to Chinese Patent Application 200880125590.3 dated May 14, 2013, along with an English language translation.
Montefiori et al. "Neutralizing and Infection-Enhancing Antibody Responses to Human Immunodeficiency Virus Type 1 in Long-Term Nonprogressors" *J. Infect. Dis.*, vol. 173, pp. 60-67, 1996.
Study of Prevalence and Control of HIV/AIDS in Asia-Pacific region and Impact on Japan, 2006, Review and shared study Report, Mar. 2007, p. 17-26.
Binley et al. "Comprehensive Cross-Clade Neutralization Analysis of a Panel of Anti-Human Immunodeficiency Virus Type 1 Monoclonal Antibodies" *J. Virol.*, vol. 78, No. 23, pp. 13232-13252, 2004.
Krachmarov et al. "Factors Determining the Breadth and Potency of Neutralization by V3-Specific Human Monoclonal Antibodies Derived from Subjects Infected with Clade A or Clade B Strains of Human Immunodeficiency Virus Type 1" *J. Virol.*, vol. 80, No. 14, pp. 7127-7135, 2006.
Gorny et al. "Human Monoclonal Antibodies Specific for Conformation-Sensitive Epitopes of V3 Neutralize Human Immunodeficiency Virus Type 1 Primary Isolates from Various Clades" *J. Virol.*, vol. 76, No. 18, pp. 9035-9045, 2002.
Tilley et al. "A Human Monoclonal Antibody Against the CD4-Binding Site of HIV1 gp120 Exhibits Potent, Broadly Neutralizing Activity" *Res. Virol.*, vol. 142, pp. 247-259, 1991.
Tilley et al. "Synergistic Neutralization of HIV-1 by Human Monoclonal Antibodies Against the V3 Loop and the CD4-Binding Site of gp120" *AIDS Res. Hum. Retroviruses*, vol. 8, No. 4, pp. 461-467, 1992.
Office Action issued with respect to Japanese Patent Application No. 2009-542577, mailed Oct. 22, 2013, along with an English language excerption.

\* cited by examiner

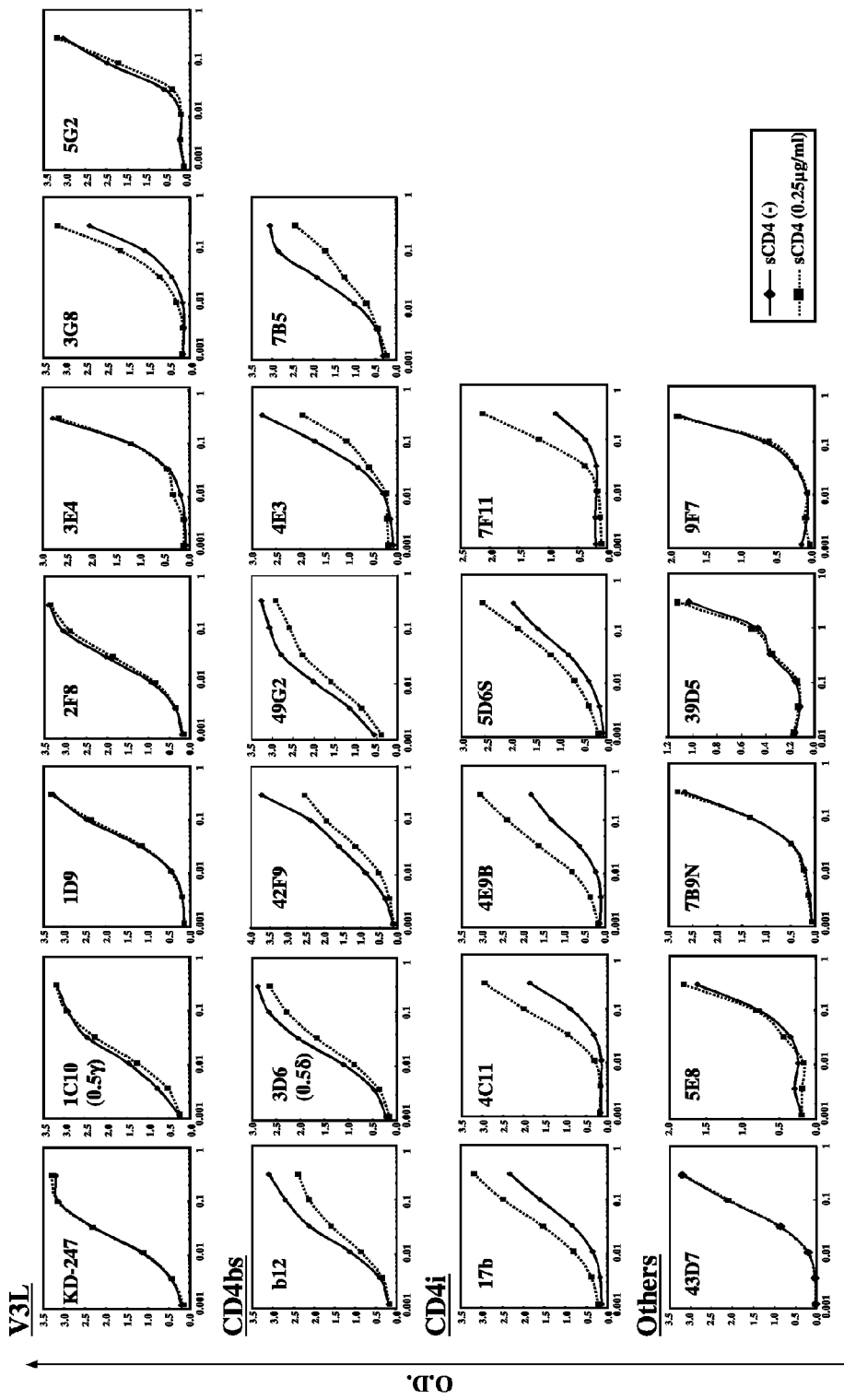
Fig.1 Analysis of the reactivity of a monoclonal antibody by gp120-capture ELISA

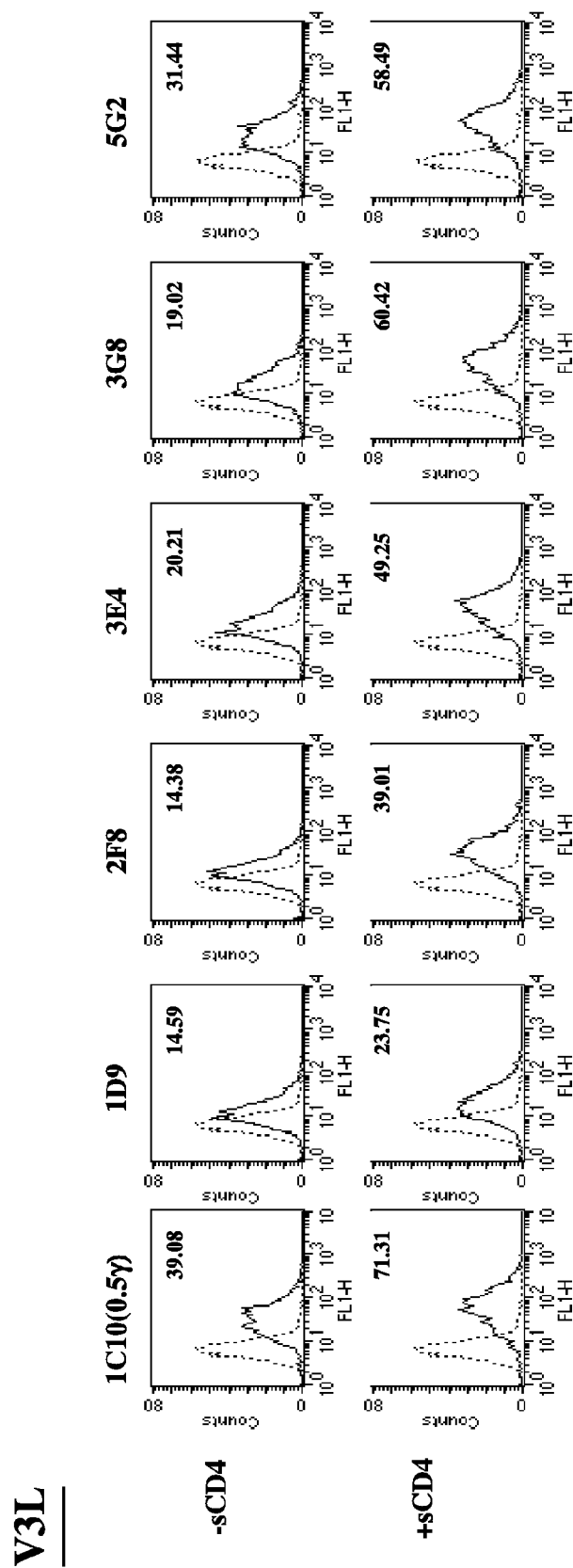
Fig.2 FACS analysis of the binding activity onto the surface of an HIV-1JR-FL chronically infected cell (PM1/JR-FL)

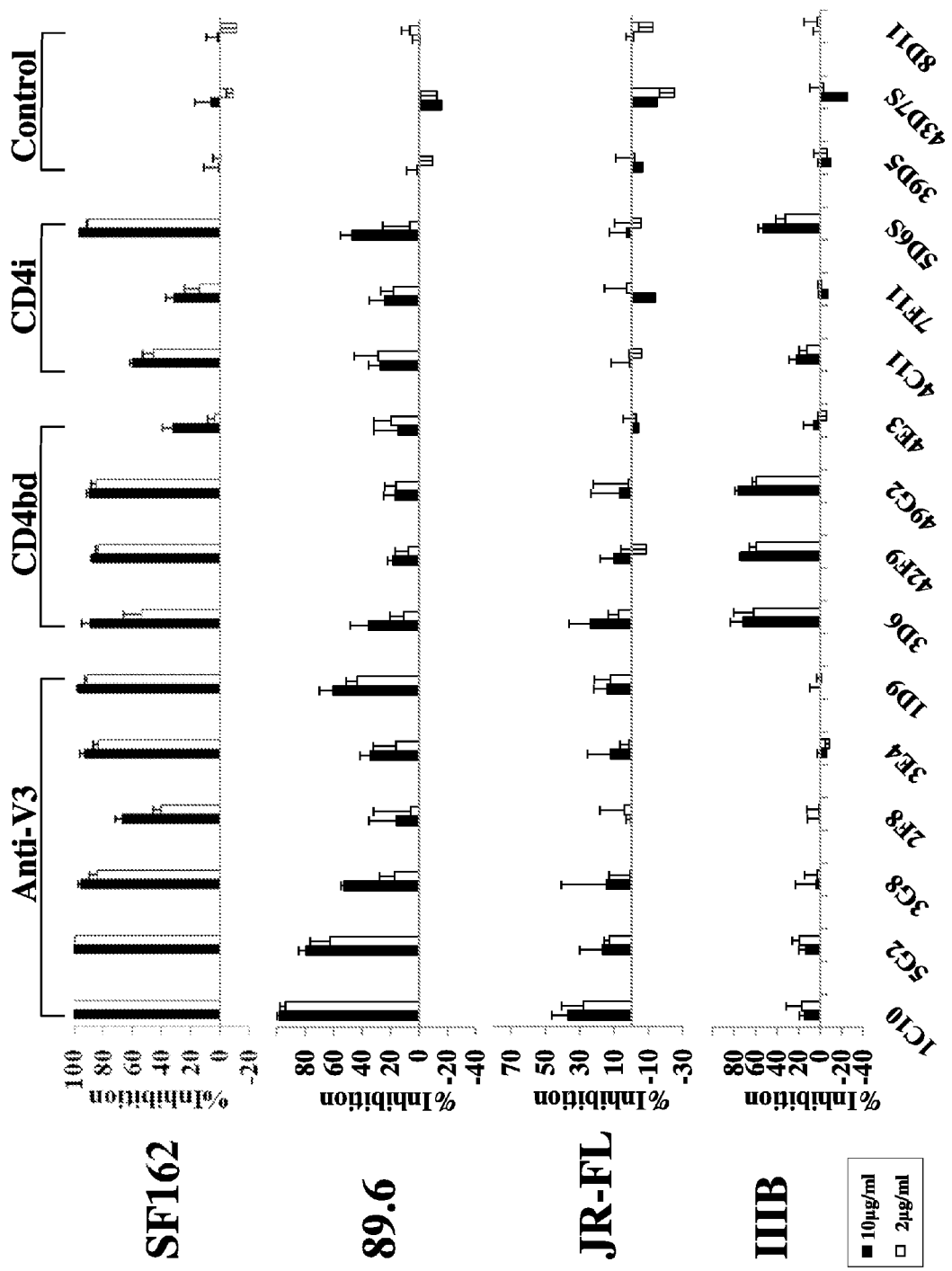

Fig.4 Significant increase in the reactivity of a V3 antibody with gp120, which is caused by 0.5d(3D6)

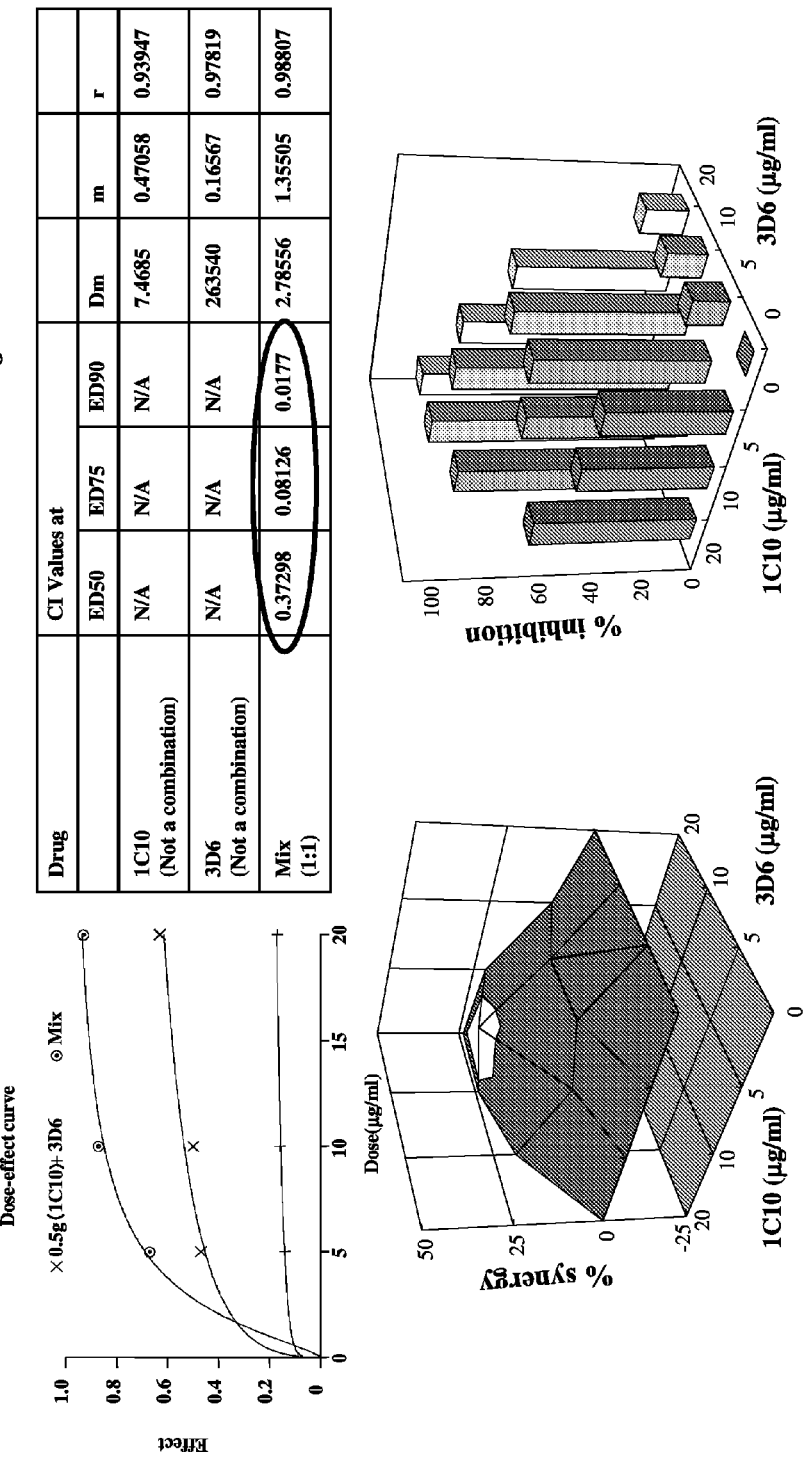
Fig. 5 Synergistic effects of 0.5γ(1C10) combined with 0.5δ (3D6) on the suppression of HIV-$1_{JR-FL}$
| Drug | CI Values at | | | | | |
|---|---|---|---|---|---|---|
| | ED50 | ED75 | ED90 | Dm | m | r |
| 1C10 (Not a combination) | N/A | N/A | N/A | 7.4685 | 0.47058 | 0.93947 |
| 3D6 (Not a combination) | N/A | N/A | N/A | 263540 | 0.16567 | 0.97819 |
| Mix (1:1) | 0.37298 | 0.08126 | 0.0177 | 2.78556 | 1.35505 | 0.98807 |
1C10 and 3D6 cover different tropism virus and also show synergy effect on the same virus.

Fig.6

1C10 VH Nuc.
GAGGTGCAGCTGGTGGAGTCTGGAGGAGGTTTGATCCAGCCTGGGGGGTCCCTGAGACTCTCCTGTGCAGCC
TCTGGGTTCACAGTCAGTAGCAGCAGCATGAGCTGGGTCCGCCAGGCTCCAGAGAAGGGGCTGGAGTGGGTC
TCAGTTGTTTATAGCGGTGGGAACACATATAACGCAGACTCCGTGAAGGGCCGATTCAGCATCTCCAGAGAC
AATTCCAAGAACACGGTATATCTTCAGATGAACAGCCTGAGAGCCGACGACACGGCCGTGTATTACTGTGCG
AGAGATTTAGGGGGGGGGACCGGTCCTCTGACTACTGGGGCCAGGGCACCCTGGTCACCGTCTCCTCA

1C10 VL Nuc.
GACATCCAGTTGACCCAGTCTCCATCCTCCCTGTCTGCATCTGTGGGAGACAGAGTCACCATCACTTGCCGG
GCAAGTGAGAGCATTAACACCTATTTAAATTGGTATCAACAGAGACCAGGGAAAGCCCCTAAACTCCTGATC
TATGCTGCATCCACTTTACAAACTGGGGTCCCATCAAGGTTCAGTGGCAGTGGGTCTGGGACACTTTTCACT
CTCACCATCAGCAGTCTGCAACCTGAGGATCTTGCAACTTATTACTGTCAACAGAGTTTCAGTACCCTCCCG
TACACTCTTGGCCGGGGGACCAAGGTGGAGATCAAAGGT

1C10 VH Amino acids sequence

|  FR1 | CDR1 | FR2 | CDR2 |
|---|---|---|---|
| EVQLVESGGGLIQPGGSLRLSCAASGFTVS | SSSMS | WVRQAPEKGLEWVS | VVYSGGNTYNADSVKG |

|  FR3 | CDR3 | FR4 |
|---|---|---|
| RFSISRDNSKNTVYLQMNSLRADDTAVYYCAR | DLGGGDRSSDY | WGQGTLVTVSS |

1C10 VL Amino acids sequence

|  FR1 | CDR1 | FR2 | CDR2 |
|---|---|---|---|
| DIQLTQSPSSLSASVGDRVTITC | RASESINTYLN | WYQQRPGKAPKLLIY | AASTLQT |

|  FR3 | CDR3 | FR4 |
|---|---|---|
| GVPSRFSGSGSGTLFTLTISSLQPEDLATYYC | QQSFSTLPYT | LGRGTKVEIKG |

Fig. 7

5G2 VH Nuc.
GAGGTGCAGCTGGTGGAGTCTGGGGGAGGCGTGGTCCGGCCTGGGAACTCCCTGAGACTCTCCTGTGCAGCC
TCTGGAATCATCTTCAGTACCGCTAATTTACACTGGCTCCGCCACGTTCCAGGCAAGGGCCTGGAGTGGGTG
GCCATTATTTCATATGATGGCCACAGACAATACTACGCAGACCTCGTGAAGGGCCGATTCACCATCTCCAGA
GACAATTCCAAGAACACCCTGCATCTGCAAATGGACGGCCTGACATCTGACGACACGGCTGTCTATTATTGT
GCGAAAGACGGGGCAGATGAGAACAATTTAGGTCCCGCCTTTGACTACTGGGGCCGGGGCACCCTGGTCACC
GTCTCCTCA

5G2 VL Nuc.
GAAATTGTGTTGACGCAGTCTCCAGCCACCCTGTCTGTATCACCAGGGGAAGGAGCCACCCTCTCCTGCAGG
GCCAGTCAGAGTATTAGCAGCAACTTAGCCTGGTACCAGCAGAAGCCTGGCCAGGCTCCCAGGCTCCTCATC
TATGGTGCATCCACCGGGGCCACTGGTATCCCAGCCAGGTTCAGTGGCAGTGGGTCTGGGACAGACTTCACT
CTCACCATCAGCAGACTGGAGCCTGAAGATTTTGCGATTTATTACTGTCAGCAGTATGGTAGTTTACCGATA
ACCTTCGGCCAAGGGACACGACTGGAGATTAAACGT

5G2 VH Amino acids sequence
```
        FR1                      CDR1      FR2
EVQLVESGGGVVRPGNSLRLSCAASGIIFS TANLH WLRHVPGKGLEWVA
      CDR2                     FR3                         CDR3
 IISYDGHRQYYADLVKG RFTISRDNSKNTLHLQMDGLTSDDTAVYYCAK DGADENNLGPAFDY
    FR4
 WGRGTLVTVSS
```

5G2 VL Amino acids sequence
```
         FR1                 CDR1         FR2       CDR2
EIVLTQSPATLSVSPGEGATLSC RASQSISSNLA WYQQKPGQAPRLLIY GASTGAT
          FR3                   CDR3         FR4
GIPARFSGSGSGTDFTLTISRLEPEDFAIYYC QQYGSLPIT FGQGTRLEIKR
```

Fig.8

3D6 VH Nuc.
GAGGTGCAGCTGGTGGAGTCTGCAGCTGAGGTGAAGAAGCCTGGGGCCTCAGTGAAGGTCTCCTGCAAGGCT
TCTGGTTACACTTTTACCAGCTATGGTATCAGCTGGGTGCGACAGGCCCCTGGACAAGGGCTTCAGTGGATG
GGATGGATCAGCGCTTACAACGGTAACACTAAGTTTGCACAAGaATTTAAGGGCAGAGTCACCATGACCACA
GACACATCCGCGACCACAGCCTACATGGAGCTGAGGAGCCTGAGATCTGACGACACGGCCGTGTATTATTGT
GCGAGGAGGAATTACTATGATTCGGGGAGTTATTATATTCGTGACGGGGACTACAGTATGGATGTCTGGGGC
CAAGGCACCCTGGTCACCGTCTCCTCA

3D6 VL Nuc.
CAGTCTGTGCTGACTCAGCCGCCCTCAGCGTCTGGGACCCCCGGGCAGAGGGTCACCATCTCTTGTTCTGGA
AGCGGCTCCAACATCGGAAGTAATACTGTAAACTGGTACCAGCAGTTCCCAGGAACGGCCCCCAAACTCCTC
ATCTATAATAATAATCAGCGGCCCTCAGGGGTCCCTGACCGATTCTCTGGCTCCAAGTCTGGCACCTCAGCC
TCCCTGGCCATCAGTGGGCTCCAGTCTGCGGATGAGGCTGATTATTACTGTGCAACATGGGATGACAGCCTG
GATGGTTGGGTGTTCGGCGGAGGGACCAAGCTGACCGTCCTAGGT

3D6 VH Amino acids sequence

```
            FR1                     CDR1        FR2              CDR2
EVQLVESAAEVKKPGASVKVSCKASGYTFT SYGIS WVRQAPGQGLQWMG WISAYNGNTKFAQ
            FR3                            CDR3                      FR4
EFKG RVTMTTDTSATTAYMELRSLRSDDTAVYYCAR RNYYDSGSYYIRDGDYSMDV WGQGTL
```

VTVSS

3D6 VL Amino acids sequence

```
            FR1                    CDR1              FR2            CDR2
QSVLTQPPSASGTPGQRVTISC SGSGSNIGSNTVN WYQQFPGTAPKLLIY NNNQRPSGVPDRFS
            FR3                CDR3          FR4
GSKSGTSASLAISGLQSADEADYYC ATWDDSLDGWV FGGGTKLTVLG
```

Fig.9

42F9 VH Nuc.
GAGGTGCAGCTGGTGGAGTCTGGGGGAGGTGTGGTACGGCCTGGGGGGTCCCTGAGACTCTCCTGTGCAGCC
TCTGGATTCGCCTTTGGTGAGTATGGCATGAGCTGGGTCCGCCAAGCTCCAGGGAAGGGGCTGGAGTGGGTC
TCTGGTATTAATTGGAATGGTGGTAGCACAGGTTATGCAGACTCTGTGCAGGGCCGATTCACCACCTCCAGA
GACAACGCCAAGAACTCCCTGTATCTGCAAATGAACAGTCTGAGAGCCGAGGACACGGCCTTGTATTACTGT
GCGAGAGATGAGAATTACGATATTTTGACTGGTAACTACTACTACGGTATGGACGTCTGGGGCCAAGGGACC
ACGGTCACCGTCTCCTC

42F9 VL Nuc.
GACATCCAGTTGACCCAGTCTCCATCCTCCCTGTCTGCATCTGTGGGAGACAGAGTCACCATCACTTGCCGG
GCAAGTCAGAGCATTAGCAACTATTTAaATTGGTATCAGCAGAAACCAGGGAAAGCCCCTAAGCTCCTGATC
TATGCTGCATCCAGTTTGCAAAGTGGGGTCCCATCAAGGTTTAGTGGCAGTGGATCTGGGACAGATTTCACT
CTCACCATCAGCAGTCTGCAACCTGAAGATTTTGCAACTTTCTACTGTCAACAGAGTCACAGTATCCCCTAC
ACTTTTGGCCAGGGGACCAAGCTGGAGATCAAACGT

42F9 VH Amino acids sequence
```
            FR1                    CDR1          FR2         CDR2
EVQLVESGGGVVRPGGSLRLSCAASGFAFG  EYGMS  WVRQAPGKGLEWVS  GINWNGG
                      FR3                         CDR3
STGYADSVQG RFTTSRDNAKNSLYLQMNSLRAEDTALYYCAR DENYDILTGNYYYGM
     FR4
DV WGQGTTVTVSS
```

42F9 VL Amino acids sequence
```
           FR1                 CDR1          FR2        CDR2
DIQLTQSPSSLSASVGDRVTITC  RASQSISNYLN  WYQQKPGKAPKLLIY  AASSLQS
          FR3                      CDR3         FR4
 GVPSRFSGSGSGTDFTLTISSLQPEDFATFYC QQSHSIPYT FGQGTKLEIKR
```

Fig.10

49G2 VH Nuc.

GAGGTGCAGCTGGTGCAGTCTGGGGCTGAGGTGAAGAAGCCTGGGGCCTCAGTGAAGGTCTCCTGCAAGGCT
TCTGGATACACCTTCACCGGCTACTATATGCACTGGGTGCGACAGGCCCCTGGACAAGGGCTTGAGTGGATG
GGATGGATCAACCCTAACAGTGGTGGCACAAACTATGCACAGAAGTTTCAGGGCAGGGTCACCATGACCAGG
GACACGTCCATCAGCACAGCCTACATGGAGCTGAGCAGGCTGAGATCTGACGACACGGCCGTGTATTACTGT
GCGAGAGGACCTATAGCAGCAGCAACCCATGCTTTTGATATCTGGGGCCAAGGGACAATGGTCACCGTCTCT
TCA

49G2 VL Nuc.

CAGTCTGTGCTGACTCAGCCACCCTCAGCGTCTGGGACCCCCGGGCAGAGGGTCACCATCTCTTGTTCTGGA
AGCGGCTCCAACATCGGAAGTAATACTGTAAACTGGTACCAGCAGTTCCCAGGAACGGCCCCCAAACTCCTC
ATCTATAATAATAATCAGCGGCCCTCAGGGGTCCCTGACCGATTCTCTGGCTCCAAGTCTGGCACCTCAGCC
TCCCTGGCCATCAGTGGGCTCCAGTCTGCGGATGAGGCTGATTATTACTGTGCAACATGGGATGACAGCCTG
gATGGTTGGGTGTTCGGCGGAGGGACCAAGCTGACCGTCCTAGGT

49G2 VH Amino acids sequence

```
              FR1                CDR1       FR2          CDR2
EVQLVQSGAEVKKPGASVKVSCKASGYTFT GYYMH WVRQAPGQGLEWMG WINPNSG
                    FR3                        CDR3
GTNYAQKFQG RVTMTRDTSISTAYMELSRLRSDDTAVYYCAR GPIAAATHAFDI WG
    FR4
QGTMVTVSS
```

49G2 VL Amino acids sequence

```
             FR1              CDR1        FR2         CDR2
QSVLTQPPSASGTPGQRVTISC SGSGSNIGSNTVN WYQQFPGTAPKLLIY NNNQRP
              FR3                  CDR3         FR4
S GVPDRFGSKSGTSASLAISGLQSADEADYYC ATWDDSLDGWV FGGGTKLTVLG
```

MONOCLONAL ANTIBODIES THAT BIND TO THE V3 LOOP OF HIV-1 GP120

BACKGROUND OF THE INVENTION

1. Technical Field

The present invention relates to a monoclonal antibody having an activity of neutralizing human immunodeficiency virus (HIV).

2. Background Art

Acquired Immunodeficiency Syndrome (AIDS) is a pathologic condition caused by chronic infection with Lentivirus called Human Immunodeficiency virus (HIV). In recent years, an antiviral agent for inhibiting the growth of HIV has been developed, and thus it has become possible to inhibit the onset of AIDS. However, even using a strong antiviral agent, it is still difficult to completely cure HIV, and the antiviral treatment needs to be continued on a lifetime basis. On the other hand, it has become clear that such antiviral agents are problematic in terms of the emergence of drug-resistant virus and chronic toxicity caused by the long-term use thereof. Accordingly, the current antiviral treatment has been still insufficient. Moreover, such antiviral agents are expensive, and thus the long-term use thereof is substantially impossible in developing countries. Under such circumstances, the development of a vaccine for prevention of HIV infection has been a worldwide issue, and also, it has been desired to develop a new therapeutic agent having no side effects.

There have been reported various monoclonal antibodies that neutralize HIV infection (Burton, D R. et al., Nat. Immunol. 5, pp. 233-236, 2004; Zolla-Pazner, S. et al., Nat. Rev. Immunol. 4, pp. 199-210, 2004; Eda, Y. et al., J. Virol. 80: 5552-5562, 2006).

Depending on their target molecules, such monoclonal antibodies are broadly classified into: antibodies against the variable region such as V1/V2 or V3 of an HIV envelope protein gp120; antibodies against the CD4-binding site (CD4bs) thereof; and antibodies against CD4i (epitope appearing after the binding of CD4-gp120). On the other hand, the neutralizing activity of an antibody against the MPR (membrane proximal region) of a transmembrane protein gp41 has also been published. Among these antibodies, antibodies that have seemed to show a cross-reaction include: 447-52D and KD-247 in the case of V3 antibodies; b12 in the case of CD4bs antibodies; 2F5 and 4E10 in the case of gp41-MPR antibodies; and 2G12 in the case of anti-gylcan antibodies. The V3 antibodies have cross-reactivity, but these antibodies have been problematic in that viral strains with which they can react are limited. On the other hand, since the gp41-MPR antibodies have had a cross-reaction with many clinically isolated strains, they have become a focus of attention over recent years. However, it has been currently reported that such antibodies cross-react with the membranelipids of host cells, and that, as a matter of fact, an autoantibody cross-reacts with the gp41 of HIV. Furthermore, b12 has a long CD3 portion consisting of 18 amino acids, and thus, its cross-reactivity with an autoantigen has been suggested (Haynes, B F et al., Science 308, pp. 1906-1908, 2005).

Non-Patent Document 1: Burton, D R. et al., Nat. Immunol. 5, pp. 233-236, 2004
Non-Patent Document 2: Zolla-Pazner, S. et al., Nat. Rev. Immunol. 4, pp. 199-210, 2004
Non-Patent Document 3: Eda, Y. et al., J. Virol. 80: 5552-5562, 2006
Non-Patent Document 4: Haynes, B F et al., Science 308, pp. 1906-1908, 2005

BRIEF DESCRIPTION OF THE DRAWINGS

FIG. 1 shows the analysis of the reactivity of a monoclonal antibody by gp120-capture ELISA.

FIG. 3 shows the cross-neutralizing activity of a neutralizing monoclonal antibody on 4 types of envelope pseudotyped viruses.

FIG. 4 shows a significant increase in the reactivity of a V3 antibody with gp120, which is caused by 0.5d(3D6).

FIG. 5 shows the synergistic effect of the combination of 0.5 g(1C10) with 0.5d(3D6) on the suppression of HIV-1JR-FL.

FIG. 6 shows the nucleotide sequence of the antigen-binding site of the monoclonal antibody 0.5γ(1C10) of the present invention, and a deduced amino acid sequence. FIG. 6 discloses SEQ ID NOS 11, 12, 1, and 2, respectively, in order of appearance.

FIG. 7 shows the nucleotide sequence of the antigen-binding site of the monoclonal antibody 5G2 of the present invention and a deduced amino acid sequence. FIG. 7 discloses SEQ ID NOS 13, 14, 3, and 4, respectively, in order of appearance.

FIG. 8 shows the nucleotide sequence of the antigen-binding site of the monoclonal antibody 0.5δ(3D6) of the present invention and a deduced amino acid sequence. FIG. 8 discloses SEQ ID NOS 15, 16, 5, and 6, respectively, in order of appearance.

FIG. 9 shows the nucleotide sequence of the antigen-binding site of the monoclonal antibody 42F9 of the present invention and a deduced amino acid sequence. FIG. 9 discloses SEQ ID NOS 17, 18, 7, and 8, respectively, in order of appearance.

FIG. 10 shows the nucleotide sequence of the antigen-binding site of the monoclonal antibody 49G2 of the present invention and a deduced amino acid sequence. FIG. 10 discloses SEQ ID NOS 19, 20, 9, and 10, respectively, in order of appearance.

DETAILED DESCRIPTION OF THE INVENTION

Figure 2:
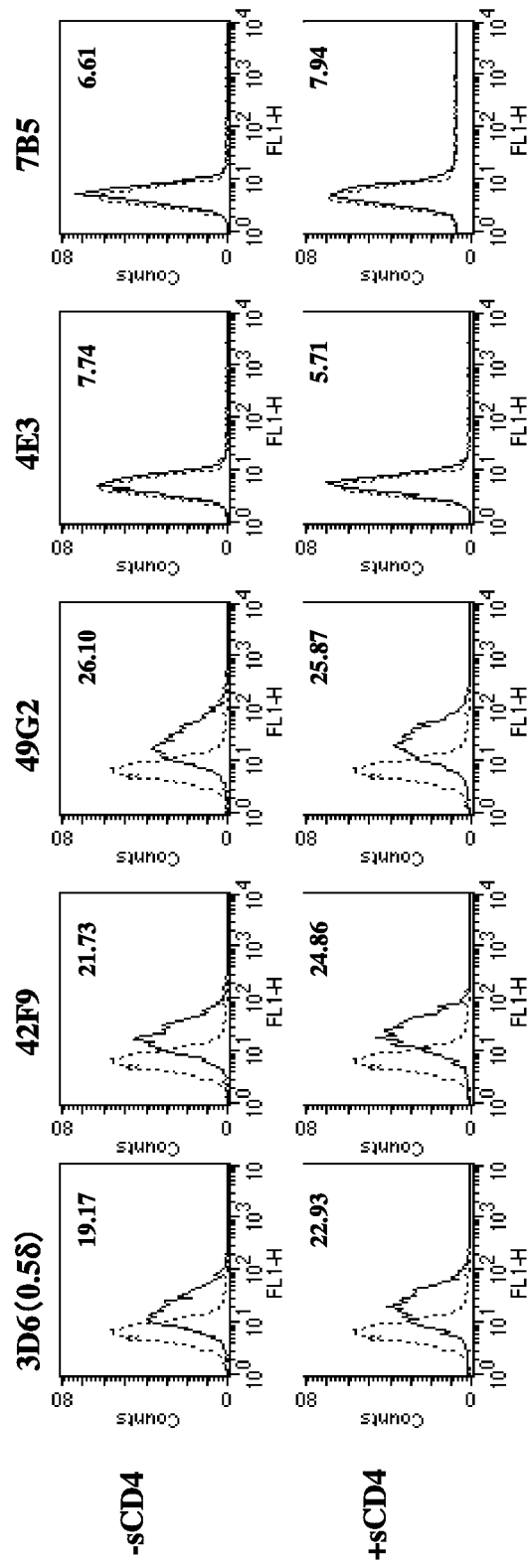
FIG. 2 shows the FACS analysis of the binding activity of each antibody onto the surface of an HIV-1JR-FL chronically infected cell (PM1/JR-FL).
Figure 2:
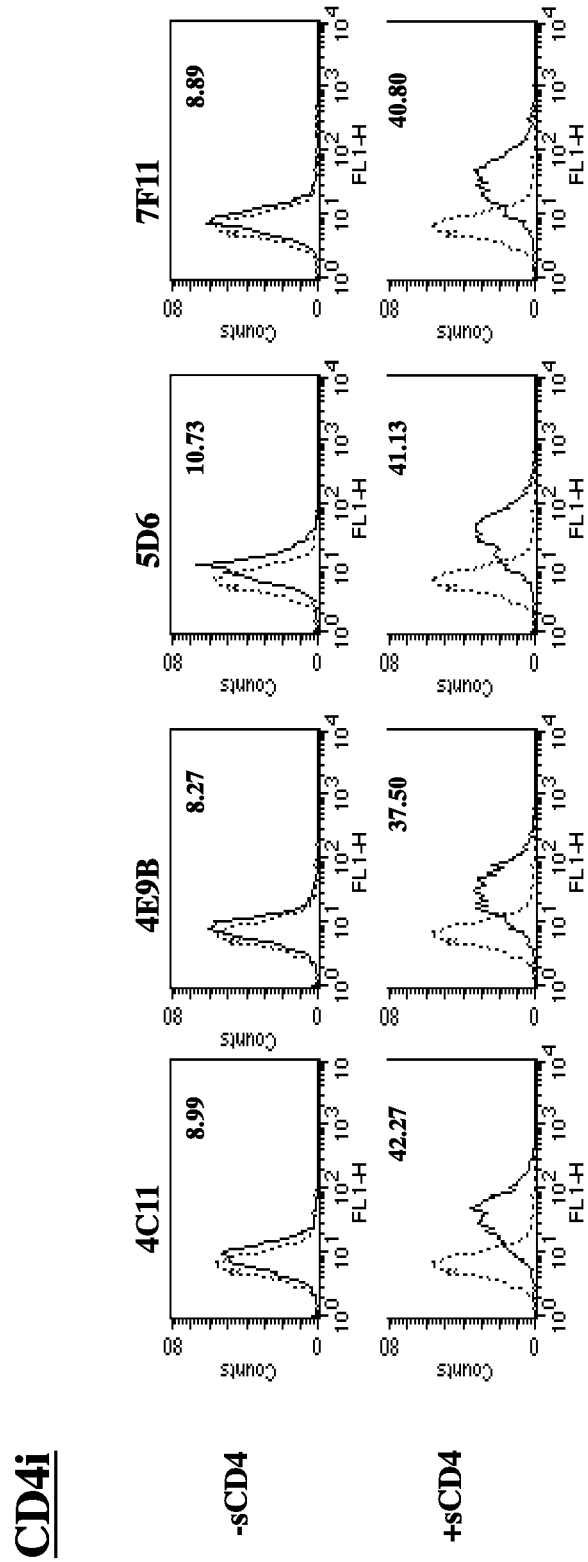
Figure 2:
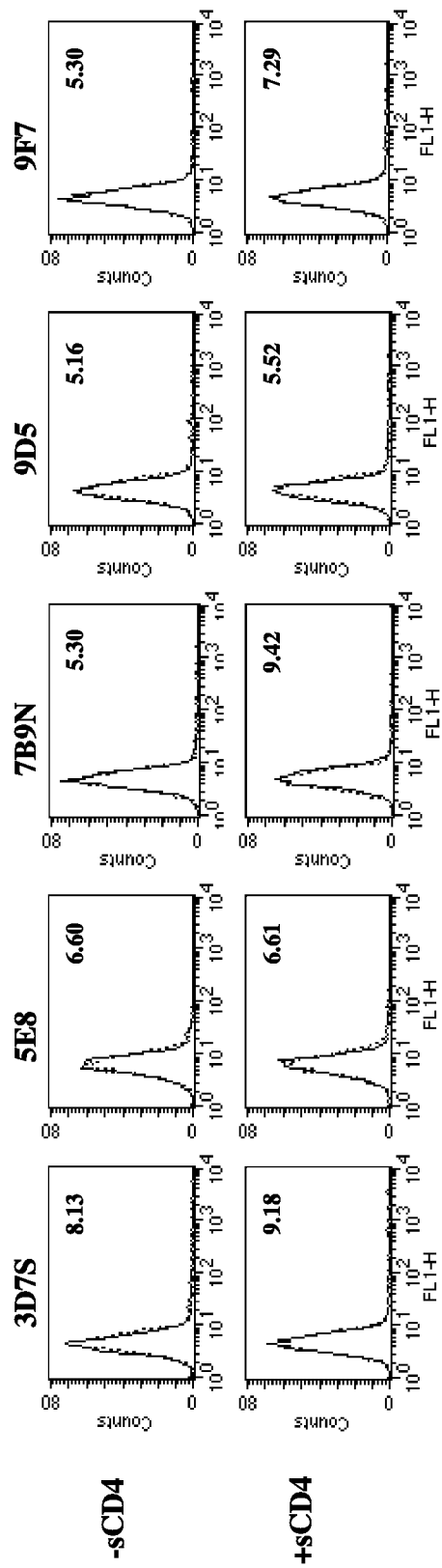
Figure 11:
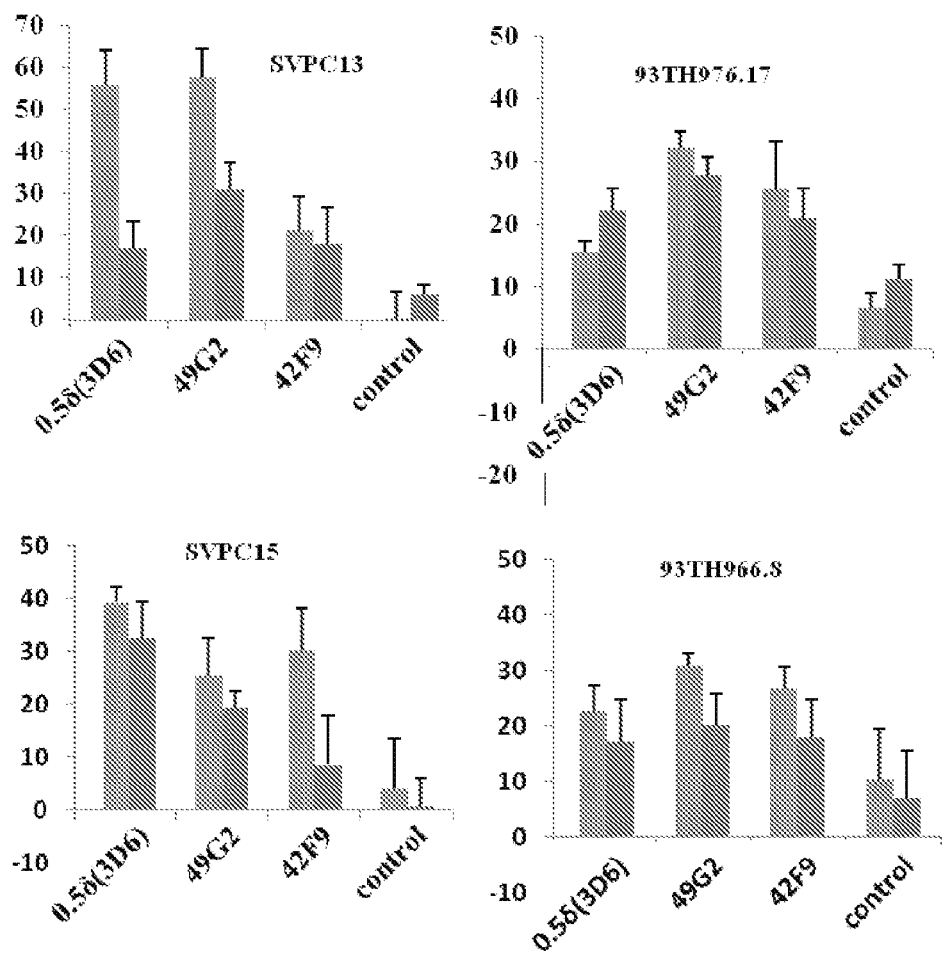
FIG. 11 shows the neutralizing activity of the antibody of the present invention on various types of viral strains.

Problems to be Solved by the Invention

It is an object of the present invention to provide a monoclonal antibody having a neutralizing activity on a wide range of HIV strains.

Means for Solving the Problems

A reason for not developing a vaccine for prevention of HIV infection is that an effective neutralizing antibody has not yet been clarified. Meanwhile, some long-term nonprogressive HIV infection cases, which have not progressed over a long period of time, exhibit a neutralizing activity on a wide range of viral strains and control the growth of viruses. In order to examine the types of neutralizing antibodies that effectively act in such long-term nonprogressive HIV infection cases in which HIV has not progressed over a long period of time, the present inventors have immortalized B cells in peripheral blood with EB virus, followed by cloning, so as to produce a monoclonal antibody-producing line. By studying the properties of the thus obtained monolconal antibody, an antiviral reaction effective for the long-term nonprogressive cases can be revealed. Moreover, the obtained monoclonal antibody can also be applied to the development of vaccines or new therapeutic agents.

Thus, the present invention provides the following invention.

(1) A monoclonal antibody that recognizes the V3 loop of the envelope glycoprotein gp120 of AIDS virus, which is any one selected from the following antibodies:
(a) an antibody having the amino acid sequence shown in SEQ ID NO: 1 as the amino acid sequence of a H chain variable region (VH), and having the amino acid sequence shown in SEQ ID NO: 2 as the amino acid sequence of a L chain variable region (VL); and
(b) an antibody having the amino acid sequence shown in SEQ ID NO: 3 as the amino acid sequence of a H chain variable region (VH), and having the amino acid sequence shown in SEQ ID NO: 4 as the amino acid sequence of a L chain variable region (VL).
(2) A monoclonal antibody that recognizes the CD4-binding site of the envelope glycoprotein gp120 of AIDS virus, which is any one selected from the following antibodies:
(a) an antibody having the amino acid sequence shown in SEQ ID NO: 5 as the amino acid sequence of a H chain variable region (VH), and having the amino acid sequence shown in SEQ ID NO: 6 as the amino acid sequence of a L chain variable region (VL);
(b) an antibody having the amino acid sequence shown in SEQ ID NO: 7 as the amino acid sequence of a H chain variable region (VH), and having the amino acid sequence shown in SEQ ID NO: 8 as the amino acid sequence of a L chain variable region (VL); and
(c) an antibody having the amino acid sequence shown in SEQ ID NO: 9 as the amino acid sequence of a H chain variable region (VH), and having the amino acid sequence shown in SEQ ID NO: 10 as the amino acid sequence of a L chain variable region (VL).
(3) A monoclonal antibody recognizing the V3 loop of the envelope glycoprotein gp120 of AIDS virus, which is produced by cells having accession No. FERM BP-11021 or accession No. FERM BP-11060, or a fragment thereof.
(4) A monoclonal antibody recognizing the CD4-binding site of the envelope glycoprotein gp120 of AIDS virus, which is produced by cells having accession No. FERM BP-11020, accession No. FERM BP-11022, or accession No. FERM BP-11023.
(5) The antibody according to any one of (1) to (4), which is produced by cells that are obtained by screening the B cells of HIV-infected patients in long-term nonprogressive HIV infection cases, in terms of binding ability to gp120, and then selecting B cells that produce gp120-binding antibodies.
(6) A method for producing the antibody of any one of (1) to (5), which comprises screening the B cells of HIV-infected patients in long-term nonprogressive HIV infection cases, in terms of binding ability to gp120, then selecting B cells that produce gp120-binding antibodies, and then collecting the antibodies produced by the selected B cells.
(7) A cell which produces the antibody of (1), having accession No. FERM BP-11021 or accession No. FERM BP-11060.
(8) A cell which produces the antibody of (2), having accession No. FERM BP-11020, accession No. FERM BP-11022, or accession No. FERM BP-11023.
(9) An agent for preventing and/or treating HIV infection, which comprises at least one monoclonal antibody selected from the antibodies of (1) to (5).
(10) An agent for preventing and/or treating HIV infection, which comprises the combination of the monoclonal antibody of (1) or (3) and the monoclonal antibody of (2) or (4).

Effects of the Invention

The monoclonal antibody of the present invention is useful as an agent for preventing and/or treating AIDS/HIV-1 infection. In addition, the monoclonal antibody of the present invention is also useful as a reagent used for studying the development of a neutralizing antibody-inducible HIV vaccine.

BEST MODE FOR CARRYING OUT THE INVENTION

Hereinafter, the embodiments and methods of the present invention will be described.
1. Monoclonal Antibody of the Present Invention A first embodiment of the present invention relates to a monoclonal antibody that recognizes the V3 loop of the envelope glycoprotein gp120 of AIDS virus, which is any one selected from the following antibodies:
(a) an antibody having the amino acid sequence shown in SEQ ID NO: 1 as the amino acid sequence of a H chain variable region (VH), and having the amino acid sequence shown in SEQ ID NO: 2 as the amino acid sequence of a L chain variable region (VL); and
(b) an antibody having the amino acid sequence shown in SEQ ID NO: 3 as the amino acid sequence of a H chain variable region (VH), and having the amino acid sequence shown in SEQ ID NO: 4 as the amino acid sequence of a L chain variable region (VL).

A specific example of the aforementioned antibody is a monoclonal antibody recognizing the V3 loop of the envelope glycoprotein gp120 of AIDS virus, which is produced by cells having accession No. FERM BP-11021 or accession No. FERM BP-11060, or a fragment thereof.

A second embodiment of the present invention relates to a monoclonal antibody that recognizes the CD4-binding site of the envelope glycoprotein gp120 of AIDS virus, which is any one selected from the following antibodies:
(a) an antibody having the amino acid sequence shown in SEQ ID NO: 5 as the amino acid sequence of a H chain variable region (VH), and having the amino acid sequence shown in SEQ ID NO: 6 as the amino acid sequence of a L chain variable region (VL);
(b) an antibody having the amino acid sequence shown in SEQ ID NO: 7 as the amino acid sequence of a H chain variable region (VH), and having the amino acid sequence shown in SEQ ID NO: 8 as the amino acid sequence of a L chain variable region (VL); and
(c) an antibody having the amino acid sequence shown in SEQ ID NO: 9 as the amino acid sequence of a H chain variable region (VH), and having the amino acid sequence shown in SEQ ID NO: 10 as the amino acid sequence of a L chain variable region (VL).

A specific example of the aforementioned antibody is a monoclonal antibody recognizing the CD4-binding site of the envelope glycoprotein gp120 of AIDS virus, which is produced by cells having accession No. FERM BP-11020, accession No. FERM BP-11022, or accession No. FERM BP-11023.

Immortalized B cells producing the monoclonal antibodies 3D6(0.58), 5G2, 42F9, and 49G2 described in the examples of the present specification were each deposited with the International Patent Organism Depositary, the National Institute of Advanced Industrial Science and Technology, an Independent Administrative Institution under the Ministry of Economy, Trade and Industry, at the AIST Tsukuba Central 6, Higashi 1-1-1, Tsukuba, Ibaraki, Japan, under accession Nos. FERM BP-11020, FERM BP-11021, FERM BP-11022, and FERM BP-11023, respectively, on Sep. 17, 2008. Immortalized B cells producing the monoclonal antibody 1C10(0.57) described in the examples of the present specification were deposited with the International Patent Organism Depositary, the National Institute of Advanced Industrial Science and Technology, an Independent Administrative Institution under the Ministry of Economy, Trade and Industry, at the AIST Tsukuba Central 6, Higashi 1-1-1, Tsukuba, Ibaraki, Japan, under accession No. FERM BP-11060 (reception No. FERM ABP-11060), on Nov. 7, 2008.

The term "antibody" is used in the present specification to include not only an entire-length antibody but also an antibody fragment. An antibody fragment is preferably a functional fragment, and examples of such antibody fragment include $F(ab')_2$ and Fab'. $F(ab')_2$ and Fab' are products obtained by treating an immunoglobulin with protease (for example, pepsin, papain, etc.). Such antibody fragment is produced by digesting an immunoglobulin before and after a disulfide bond existing between two H chains in a hinge region. Further, when the term "antibody fragment" is used, it also includes a protein containing an antigen-binding site derived from a gene encoding the antibody.

For example, if IgG1 is treated with papain, it is cleaved at a site upstream of a disulfide bond existing between two H chains in a hinge region, so as to produce two homologous antibody fragments, in which a L chain fragment consisting of VL (a L chain variable region) and CL (a L chain constant region) binds to a H chain fragment consisting of VH (a H chain variable region) and CHγ1 (a γ1 region in a H chain constant region) via a disulfide bond in a C-terminal region. Each of these two homologous antibody fragments is referred to as Fab'. On the other hand, if IgG is treated with pepsin, it is cleaved at a site downstream of a disulfide bond existing between two H chains in a hinge region, so as to produce an antibody fragment that is slightly larger than the above-mentioned two Fab' fragments that bind to each other at a hinge region. This fragment is referred to as $F(ab')_2$.

Moreover, the monoclonal antibody of the present invention can be used as an immobilized antibody that is immobilized on an insoluble carrier such as a solid phase carrier, or as a labeled antibody that is labeled with a labeling substance. Such immobilized antibody and labeled antibody are all included in the scope of the present invention.

The term "immobilized antibody" is used to mean an antibody that is in a state in which the antibody is supported on an insoluble carrier via physical adsorption, chemical bond, etc. Such immobilized antibody can be used to detect, quantify, separate, or purify an antigen contained in a sample (for example, a body fluid sample such as plasma, a culture supernatant, a centrifuged supernatant, etc.). Examples of an insoluble carrier that can be used to immobilize the antibody include: (1) a plastic consisting of a polystyrene resin, a polycarbonate resin, a silicon resin, a nylon resin or the like; a plate consisting of a substance insoluble in water, such as a glass as a typical example; a product having an inner volume, such as a test tube or a tube; beads, a ball, a filter, or a membrane; and (2) insoluble carriers used in affinity chromatography, such as a cellulose carrier, an agarose carrier, a polyacrylamide carrier, a dextran carrier, a polystyrene carrier, a polyvinyl alcohol carrier, a polyamino acid carrier, or a porous silica carrier.

The term "labeled antibody" is used to mean an antibody that is labeled with a labeling substance. Such labeled antibody can be used to detect or quantify an antigen contained in a sample (for example, a body fluid sample such as plasma, a culture supernatant, a centrifuged supernatant, etc.). The type of a labeling substance that can be used in the present invention is not particularly limited, as long as it is able to bind to an antibody via a physical bond, a chemical bond, etc., so as to detect the presence thereof. Specific examples of such labeling substance include an enzyme, a fluorescent substance, a chemoluminescent substance, biotin, avidin, and a radioisotope. More specific examples of such labeling substance include: enzymes such as peroxidase, alkaline phosphatase, β-D-galactosidase, glucose oxidase, glucose-6-phosphate dehydrogenase, alcohol dehydrogenase, malate dehydrogenase, penicillinase, catalase, apoglucose oxidase, urease, luciferase or acetylcholine esterase; fluorescent substances such as fluorescein isothiocyanate, phycobiliprotein, rare earth metal chelate, dansyl chloride or tetramethyl-rhodamine isothiocyanate; radioisotopes such as $^3H$, $^{14}C$, $^{125}I$ or $^{131}I$; and biotin, avidin or chemoluminescent substances. As a method for binding a labeling substance to an antibody, a known method such as a glutaraldehyde method, a maleimide method, a pyridyl disulfide method or a periodic acid method can be used.

Herein, a radioisotope and a fluorescent substance are able to generate detectable signals by themselves. On the other hand, since an enzyme, a chemoluminescent substance, biotin, and avidin are not able to generate detectable signals by themselves, they react with one or more types of other substances, and as a result, they generate detectable signals. For example, an enzyme needs at least a substrate, and thus various types of substrates are used depending on the type of a method for measuring enzyme activity (a colorimetric method, a fluorescence method, a bioluminescence method, a chemoluminescence method or the like). In addition, in the case of biotin, it is generally allowed to react with at least avidin or enzyme-modified avidin. Various types of coloring substances are further used, depending on the above-mentioned substrates, as necessary.

2. Cell that Produces Monoclonal Antibody of the Present Invention

The present invention also relates to a cell that produces the above-described monoclonal antibody of the present invention. The monoclonal antibody of the present invention can be produced using such cell. A method for obtaining a cell that produces the monoclonal antibody of the present invention will be described below.

Lymphocytes including B lymphocytes are recovered from the peripheral blood of an HIV-infected patient by an ordinary densitometric centrifugation method or the like, and the recovered lymphocytes are then transformed with EBV in order to obtain from the lymphocytes a cell line that stably produces an antibody and continuously grows without limitations. EBV is a virus capable of transforming normal human B lymphocytes to a proliferative cell line (Nature, Vol. 269, P. 410 (1973)). As an EBV-containing material, a marmoset cell line B95-8 (Proc. Natl. Acad. Sci., USA, Vol. 87, pp. 3333-3337 (1990)) can be used. First, using a heparin-containing blood collecting tube, peripheral blood is collected from a long-term nonprogressive HIV-infected patient who has a neutralizing activity on a wide range of HIV strains, and a peripheral blood mononuclear cell (PBMC) fraction is then collected from the peripheral blood according to a densitometric centrifugation method or the like. From the obtained PBMC, CD8 positive cells are depleted according to immunomagnetic separation using Dynabeads. The CD8-depleted PBMC was suspended in a medium (15% fetal calf serum; FCS-containing RPMI1640) that contains 50% culture supernatant of the EB virus-producing cell line B95-8 (ATCC), and the resultant is then transferred to a 24-well culture dish (Linbro, ICN). Thereafter, it is cultured at 37° C. in a 5% $CO_2$-containing incubator for 12 to 18 hours. During this culture operation, B cells in the peripheral blood are infected with the EB virus, and as a result, immortalized cells can be obtained at a rate of 1 strain/$10^4$ cells. A culture supernatant of growing cells is recovered, and the recovered cells are then screened by a gp120-capture assay. With regard to clones that are repeatedly determined to be positive as a result of the screening operation, the cells are cloned by a limiting dilution method, using cells obtained by applying X-ray to the PBMC of a healthy person as feeder cells, and as a result, antibody-producing cells that have an anti-gp120 activity can be separated. If necessary, such cloning procedures are repeatedly carried out.

By culturing the thus obtained EBV-transformed cell line, the monoclonal antibody of the present invention of interest can be obtained from the cells. The antibody in the culture solution is purified, for example, by appropriately combining known methods such as DEAE anion exchange chromatography, affinity chromatography, an ammonium sulfate fractionation method, a PEG fractionation method, and an ethanol fractionation method, as necessary.

3. Gene of the Antibody of the Present Invention

A gene encoding the antibody of the present invention can be obtained by producing a cDNA library using mRNA derived from the above-described EBV-transformed human cells that produce the monoclonal antibody of the present invention, and then isolating a plasmid containing cDNA encoding the monoclonal antibody of the present invention from them. The above-mentioned mRNA can be prepared by culturing the EBV-transformed cells and then dissolving the cells in a guanidinium isothiocyanate solution, followed by extraction. Thereafter, cDNA is produced using the obtained mRNA as a template, and the cDNA is then incorporated into a vector, so as to produce a cDNA library. Using this cDNA library, a gene encoding the monoclonal antibody of the present invention can be obtained.

Moreover, since the nucleotide sequence and amino acid sequence of such gene encoding the antibody of the present invention have been determined in the following examples, the gene encoding the antibody of the present invention can also be produced by applying a chemical synthesis method of genes which is known to persons skilled in the art. For example, in the case of genes each comprising suitable nucleotide sequences encoding the amino acid sequences shown in SEQ ID NOS: 1 and 2, and nucleotide sequences complementary thereto, such genes are divided into several oligonucleotides, they are then chemically synthesized, and they are successively ligated to one another, as appropriate, in each block, thereby producing the gene encoding the antibody of the present invention.

The gene encoding the monoclonal antibody of the present invention is inserted into an expression vector, so as to construct a recombinant expression vector. In general, an expression vector has a promoter region upstream of a translation start codon (ATG) and also has a poly(A) signal region downstream of a translation stop codon (TAA, TGA or TAG). A recombinant expression vector is introduced into host cells according to a known method, and the thus transformed host cells are then cultured, so that the monoclonal antibody of the present invention can be expressed. As such host cells, *Escherichia coli*, yeast, animal cells, or the like can be used. By culturing the transformed host cells, the monoclonal antibody of the present invention can be produced in the culture.

4. Medicament Comprising the Monoclonal Antibody of the Present Invention

Using a pharmaceutically acceptable suitable carrier, excipient, diluent and the like, as necessary, the monoclonal antibody of the present invention can be used as an agent for preventing and/or treating HIV infection. As such agent for preventing and/or treating HIV infection, the monoclonal antibody of the present invention can be formulated in the form of an injection, for example. The dosage of the agent for preventing and/or treating HIV infection depends on the degree of symptoms, age, and body weight of a patient, an administration method, and the like. The weight of the antibody used as an active ingredient is generally from approximately 10 ng to approximately 100 mg/kg of body weight.

5. Detection of Epitope of HIV Virus Using the Monoclonal Antibody of the Present Invention According to the present invention, it is also possible to detect HIV by carrying out an immunoassay using the monoclonal antibody of the present invention or a fragment thereof. This method preferably comprises at least the following steps (a) and (b):

(a) a step of allowing the monoclonal antibody of the present invention or a fragment thereof to react with a sample; and
(b) a step of allowing the antigen-antibody complex formed in the step (a) to react with a labeled antibody used for detection.

As the detection and/or quantification method of the present invention, any method may be applied, as long as it is an assay using an antibody, namely, an immunoassay. Examples of the present detection and/or quantification method include an enzyme-linked immunosorbent assay (ELISA), a fluorescent immunoassay, a radioimmunoassay (RIA), a luminescent immunoassay, an enzyme antibody technique, a fluorescence antibody technique, an immunonephelometry, a latex agglutination reaction, a latex turbidimetry method, a hemagglutination, a particle agglutination, and a Western blotting method.

When the detection method of the present invention is carried out by applying an immunoassay method using a labeled antibody, such as an enzyme-linked immunosorbent assay, a fluorescent immunoassay, a radioimmunoassay or a luminescent immunoassay, it can also be carried out by a sandwich method or a competition method. In the case of such sandwich method, it may be adequate if at least one of a solid-phased antibody and a labeled antibody is the monoclonal antibody of the present invention.

When the antibody is used in a state in which it is sensitized to a solid phase carrier, examples of a solid phase carrier that can be used herein include particles consisting of materials such as polystyrene, a styrene-butadiene copolymer, a (meth) acrylic acid ester polymer, latex, gelatin, a liposome, a microcapsule, erythrocyte, silica, alumina, carbon black, a metallic compound, metal, ceramic, or a magnetic body.

As a sensitization method, a known method such as a physical adsorption method, a chemical bond method, or the combined use of these methods may be applied. Measurement operations may be carried out in accordance with known methods. When the measurement is carried out by an optical method, for example, a sample is allowed to react with an antibody, or a sample is allowed to react with an antibody that has been sensitized to a solid phase carrier, and a transmitted light or a scattering light is then measured by an end point method or a rate method.

When the measurement is carried out by visual observation, a sample is allowed to react with an antibody that has been sensitized to a solid phase carrier in a vessel such as a plate or a microtiter plate, and thereafter, the reaction product that is in an agglutinated state is visually observed. Instead of carrying out the measurement by visual observation, it may also be possible to carry out the measurement using an apparatus such as a microplate reader.

The present invention will be more specifically described in the following examples. However, these examples are not intended to limit the scope of the present invention.

EXAMPLES

Example 1

Production of Neutralizing Monoclonal Antibody

Peripheral blood B cells were infected with EB virus, and a cloning operation was then repeatedly carried out, so as to separate antibody-producing cells having an anti-gp120 activity. This cell production method was basically created by modifying a method that we had applied to a human T-cell leukemia virus type 1 (HTLV-1) infection case (Matsushita S., et al., Proc. Natl. Acad. Sci. (USA) 83: 3672-3676, 1986). Peripheral blood was collected from a long-term nonprogressive HIV-infected patient who had a neutralizing activity on a wide range of viral strains, and it was placed in a heparin-containing blood collecting tube (20 to 30 ml). Thereafter, a peripheral blood mononuclear cell (PBMC) fraction was isolated by a density-gradient centrifugation method using Ficoll-Hypaque. From the obtained PBMC, CD8 positive cells were depleted according to immunomagnetic separation using Dynabeads. Specifically, PBMC was incubated with Dynabeads CD8 for 1 hour at 4° C., and the magnetic beads were depleted with a magnetic device, so as to obtain CD8-depleted PBMC. The CD8-depleted PBMC (1 to $10 \times 10^6$) was suspended in 2 to 5 ml of a medium (15% fetal calf serum; FCS-containing RPMI1640) that contained 50% culture supernatant of the EB virus-producing cell line B95-8 (ATCC), and the resultant was then transferred to a 24-well culture dish (Linbro, ICN). Thereafter, it was cultured at 37° C. in a 5% $CO_2$-containing incubator for 12 to 18 hours. During this culture operation, B cells in the peripheral blood were infected with the EB virus, and as a result, immortalized cells were considered to be obtained at a rate of 1 strain/$10^4$ cells. The cultured cells were gathered and were then centrifuged, and the old medium was discarded. The CD8-depeleted PBMC was dispensed in a fresh medium on a 96-well flat bottom culture plate (Falcon), such that the PBMC concentration could be $1 \times 10^4$ or less per well. The obtained mixture was further cultured at 37° C. in a 5% $CO_2$-containing incubator. While exchanging a half amount of the medium with a fresh one every 7 to 10 days, the growth of a B cell line was waited. The growing cells were expanded on a 48-well or 24-well culture dish (Linbro, ICN). A culture supernatant of the growing cells was recovered, and it was then screened by the later-mentioned "gp120-capture assay." With regard to clones that were repeatedly determined to be positive as a result of the screening operation, the cells were cloned by a limiting dilution method, using cells obtained by applying X-ray to the PBMC of a healthy person as feeder cells, and antibody-producing cells that had an anti-gp120 activity were separated. If necessary, such cloning procedures were repeatedly carried out.

Example 2 gp120-Capture ELISA

The "gp120-capture ELISA" was applied to screen for the antibody-producing cells having an anti-gp120 activity (J. P. Moore et al., J. Virol. 67, pp. 6136-6151, 1993). Specifically, on the day before the experiment, 50 µl of anti-gp120-05 sheep antibody (D7324; Aalto Bioreagents, Dublin, Ireland) whose concentration had been adjusted to be 13.3 µg/ml with the addition of a CC buffer (Carbonate-bicarbonate buffer; pH 9.6) was added to a 96-well polypropyren plate (Falcon), and it was then left at rest at 4° C. overnight. Thereafter, a supernatant was removed, and 175 µl of a blocking buffer (2% bovine serum albumin; BSA, 0.1% Azide, PBS, pH 7.2) was added to the residue. The obtained mixture was left at rest at room temperature for 30 minutes. Thereafter, the well was washed with an ELISA wash buffer (0.15% Tween20, PBS, pH 7.2) three times, and 50 µl each of monomeric gp120 (gp120-SF2; Austral Biologicals, San Ramon, Calif.) was then added thereto. The obtained mixture was left at rest at room temperature for 2 hours. Thereafter, the resultant was washed with the ELISA wash buffer three times, so as to produce a "gp120-captured plate." A culture supernatant of B cells was added to this plate, and the mixture was then reacted at room temperature for 2 hours. The resultant was washed with the ELISA wash buffer three times, and 100 µl of anti-human IgG-ALP, which had been diluted by a factor of 1000 with the ELISA buffer, was then added to the resultant. The obtained mixture was left at rest at room temperature for 1 hour. The resultant was washed with the ELISA wash buffer three times. Phosphatase substrate (SIGMA) was dissolved in a substrate buffer (Diethanol amine buffer; pH 9.85), and 100 µl of the obtained solution was then added to each well, followed by leaving the mixture at rest at room temperature for 10 to 30 minutes. Thereafter, the absorbance (405 nm) was measured with a microplate reader. Thus, 20 types of B cell clones capable of producing gp120-bound antibodies (Table 1).

TABLE 1

List of neutralizing monoclonal antibodies which were obtained from long-term nonprogressive HIV-infected patient

| No | Clone | subclass | Traget |
|----|-------|----------|--------|
| 1  | 0.5γ(1C10) | Ig G1 κ | V3L |
| 2  | ID9 | Ig G2 κ | V3L |
| 3  | 2F8 | Ig G1 λ | V3L |
| 4  | 3E4 | Ig G2 κ | V3L |
| 5  | 3G8 | Ig G2 κ | V3L |
| 6  | 5G2 | Ig G1 κ | V3L |
| 7  | 0.5δ(3D6) | Ig G1 λ | CD4bs |
| 8  | 4E3 | Ig G1 κ | CD4bs |
| 9  | 7B5 | Ig G2 λ | CD4bs |
| 10 | 42F9 | Ig G1 κ | CD4bs |
| 11 | 49G2 | Ig G1 λ | CD4bs |
| 12 | 4C11 | Ig G2 λ | CD4i |
| 13 | 4E9B | Ig G2 κ | CD4i |
| 14 | 5D6S12 | Ig G2 κ | CD4i |
| 15 | 7F11 | Ig G2 κ | CD4i |
| 16 | 5E8 | Ig G2 κ | ND |
| 17 | 7B9N | Ig G3 κ | ND |
| 18 | 9F7 | Ig G1 κ | ND |
| 19 | 39D5 | Ig G3 κ | ND |
| 20 | 43D7 | Ig G2 κ | ND |

Example 3

Classification of Monoclonal Antibodies

Antibodies reacting with gp120 are classified into the following 4 types, depending on the types of reactive epitopes. Specifically, the 4 types are a CD4-binding site (CD4bs), a CD4-induced epitope (CD4i), a third variable loop (V3loop; V3L), and those that cannot be classified into the aforementioned groups (other epitopes). Whether or not an antibody binds to V3L is determined by ELISA using a synthetic peptide having the amino acid sequence of V3L (V3-peptide ELISA). In this experiment, we used the V3 sequence from JR-FL strain (NNT20; NNTRISIHIGPGRAFVTIGK (SEQ ID NO: 21)), which was the closest to the V3 sequence of the virus of a case from which the antibody was derived. On the day before the experiment, 100 µl of a peptide (NNT20) diluted in PBS at a concentration of 5 µg/ml was added to each well of a 96-well polypropyren plate, and it was then left at 4° C. overnight. After washing, 175 µl of a blocking buffer was added to each well, and was incubated at room temperature for 30 minutes. The plate was washed with an ELISA wash buffer three times, and a B cell culture supernatant diluted serially was then added to the wells. The plate was reacted at room temperature for 2 hours. Thereafter, the plate was washed with the ELISA wash buffer three times, and the resultant was then reacted with 100 µl of anti-human IgG-ALP for 1 hour. After washing the resultant, color was developed using ALP-Substrate, and the absorbance (405 nm) was then measured. V3-peptide ELISA was performed on the obtained 20 types of antibodies. As a result, it was found that 6 types of antibodies had reactivity with V3-peptide.

On the other hand, soluble CD4 (sCD4; R&D Systems, Inc. Minneapolis, Minn.) exerts completely opposite influences on a CD4bs antibody and a CD4i antibody. Namely, the reactivity of the CD4bs antibody is suppressed in the presence of sCD4. In contrast, the reactivity of the CD4i antibody with gp120 is enhanced in the presence of sCD4. Utilizing this property, monoclonal antibodies were classified. The "gp120-captured plate" was prepared by the same procedures as those for the above-mentioned gp120-capture ELISA. Serially diluted monoclonal antibodies were reacted in the presence or absence of 0.5 µg/ml sCD4 for 2 hours, and they were then washed with an ELISA wash buffer three times. Thereafter, the resultant antibodies were allowed to each react with 100 µl of anti-human IgG-ALP for 1 hour. After washing them, color was developed using ALP-Substrate, and the absorbance (405 nm) was then measured. As shown in FIG. 1, all of the V3 antibodies including KD-247 used as a control were not influenced by sCD4. The binding activity of five types of clones (0.5δ(3D6), 42F9, 49G2, 4E3, and 7B5) was suppressed in the presence of sCD4 (wherein b12 was used as a control). In contrast, the reactivity of four types of clones (4C11, 4E9B, 5D6S, and 7F11) was enhanced in the presence of sCD4 (wherein 17b was used as a control). There were five types of clones, which exhibited no reactivity in the V3-peptide ELISA and were not influenced by sCD4. It could not be confirmed that these clones had epitope specificity (other epitopes).

Example 4

Binding Activity to Functional Envelope

It has been known that HIV-1 has a functional envelope causing membrane fusion with target cells on viral particles and on the surfaces of chronically infected cells. In order to study whether or not the produced antibody is able to recognize this functional envelope, the binding activity of the antibody to the cell surface of HIV-1$_{JR-FL}$ chronically infected cells (PM1/JR-FL) was examined with a flow cytometer. Moreover, whether or not sCD4 had an influence on this reactivity was also examined. PM1/JR-FL cells ($2 \times 10^5$) were placed in a test tube. Thereafter, 50 µl of sCD4 that had been diluted with a FACS buffer (2% BSA, 0.02% Azide in PBS; pH 7.23) and adjusted to a concentration of 1 µg/ml, or 50 µl of only the FACS buffer, was added to the test tube. The mixture was reacted for 15 minute. Thereafter, 50 µl of monoclonal antibody diluted with a FACS buffer to a concentration of 1 to 3 µg/ml was then added to the reaction mixture, and the obtained mixture was reacted at room temperature for 45 minutes. The resultant was washed with a FACS buffer two times, and 50 µl of FITC-bound anti-human IgG antibody (Sigma) diluted with a FACS buffer at a ratio of 1:200 was then added to the resultant. The mixture was incubated at 4° C. in a dark place for 30 minutes. Thereafter, the resultant was washed with a FACS buffer two times, and it was then fixed with 0.5 ml of fixing solution {2% (w/v) paraformaldehyde in PBS}. The fixed sample was analyzed with FACSCalibur (Beckton-Dickinson). The incorporated data was analyzed with Cell Quest (Beckton-Dickinson). As shown in FIG. 2, it was found that the 5 types of V3L antibodies all had a clear binding activity to the infected cell surface. Moreover, such binding activity was enhanced in the presence of sCD4. When compared with the four clones, 1D9, 2F8, 3E4 and 3G8, 1C10(0.5γ) and 5G2 had strong reactivity in the absence of sCD4. Among antibodies classified into CD4bs, 3D6(0.5δ), 42F9 and 49G2 had a binding activity to the infected cell surface. However, 4E3 and 7B5 did not have such binding activity. Differing from the reaction with the gp120 monomer, in the case of a functional envelope consisting of a trimer, the binding inhibition of CD4bs antibodies by sCD4 was not observed. On the other hand, with regard to CD4i antibodies, the 4 types of antibodies all had only weak reactivity in the absence of sCD4, but in the presence of sCD4, such reactivity was increased up to the level equivalent to the reactivity of a V3 antibody. All of the 5 types of antibodies whose epitopes had not been identified did not have a binding activity to the infected cell surface.

Example 5

Purification of Neutralizing Antibody and Studies Regarding Neutralizing Activity With regard to 20 types of antibodies, their binding activity to the cell surface, the amount of antibody produced, and the like were taken into consideration. As a result, regarding 15 types of antibodies, the number of cells was increased, a culture supernatant was collected and was then filtered, and a monoclonal antibody was then purified using a protein A column or protein G column (GE Healthcare). The neutralizing activity of the thus purified monoclonal antibody on pseudotyped HIV-1 viruses was examined at an antibody concentrations of 10 µg/ml and 2 µg/ml, using the envelopes of 4 types of HIV-1 strains commonly used in laboratories (FIG. 3). In order to produce such pseudotyped virus, on the day before transfection, 293T cells were dispersed on a 100-mm collagen-coated plate (IWAKI) to a cell concentration of $4 \times 10^6$, and they were then cultured at 37° C. overnight. Thereafter, 5 µg of pNL4-3-Luc-E$^-$R$^-$ or 5 µg of pSG3ΔEnv (Li M. et. al, J. Virol. 79, pp. 10108-10125, 2005), 4.5 µg of an envelope expression vector, and 0.5 µg of a pRSV-REV vector were introduced into the culture using Effectene (QIAGEN), and the obtained mixture was then cultured at 37° C. in 5% $CO_2$. Twenty-four hours after initiation of the culture, a supernatant was recovered and was then pass through a 0.2-µm filter. Thereafter, it was then dispensed and was then conserved at −80° C. The obtained pseudotyped virus was subjected to a p24 Antigen ELISA kit (ZeptoMetrix Co.) to measure the amount of p24 antigen. A single-round neutralization experiment using the pseudotyped virus was carried out as follows. On the day before the experiment, GHOST-hi5 cells or TZM-bl cells were dispersed on a 96-well flat bottom culture plate (Falcon) at a concentration of $2 \times 10^4$ cells/200 µl. When the cells have grown to approximately 70% confluency, 200-500 $TCID_{50}$ pseudotyped virus and the antibody in each concentration were mixed with DMEM that contained 10% fetal calf serum (FCS), 0.1 mg/ml G418, 0.05 mg/ml Hygromycin-B, 5 µg/ml Puromycin, and 20 µg/ml Polybrane (in the case of GHOST-hi5), or contained 10% FCS, 10 µg/ml DEAE-dextran (Pharmacia Biotech; in the case of TZM-bl). The obtained mixture was left at rest on ice for 15 minutes. Thereafter, 100 µl of the antibody/virus mixed solution was added to target cells, from which the culture solution had been removed, and the obtained mixture was incubated at 37° C. in 5% $CO_2$ for 2 hours, so that the virus was adsorbed on the target cells. Thereafter, 100 µl of the aforementioned DMEM containing antibiotics and the like was further added thereto, and the mixture was then cultured at 37° C. in 5% $CO_2$ for 2 days. Thereafter, a supernatant was removed, and the residue was then washed with PBS (pH 7.4) three times. Then, 30 µl of a lysing buffer (Luc PGC50; TOYO INK MFG CO., LTD. (in the case of GHOST-hi5)) diluted by a factor of 5 with PBS, or a lysing solution (Applied Biosystems (in the case of TZM-bl)), was added to the resultant, and the obtained mixture was then shaken for 15 minutes. Thereafter, 20 µl out of the reaction solution was transferred to a plate used for luminescent measurement (Coster 3912), and 100 µl of a luciferase substrate (PicaGene; TOYO INK MFG CO., LTD.) was then added thereto. Ten seconds after the addition of the luciferase substrate, fluorescence intensity was measured with a TR477 microplate luminometer (Applied Biosystems) (in the case of GHOST-hi5). In the case of the TZM-bl cells, after the reaction solution had been transferred to the plate used for luminescent measurement, 100 µl of Galacto-Star (Applied Biosystems) diluted by a factor of 50 with a reaction buffer diluent was added thereto, and the obtained mixture was then left at rest for 1 hour in a dark place. Thereafter, β-galactosidase activity was measured with the TR477 microplate luminometer. Neutralizing activity was calculated in accordance with the expression $\{1-(t-c)/(n-c)\} \times 100$ (t: the fluorescence intensity of a sample; c: the background fluorescence intensity of only cells; n: the fluorescence intensity of a sample with no antibodies). The experiment was carried out triplicate at the same antibody concentration. An independent experiment was repeatedly carried out 2 or 3 times each.

The obtained results are shown in FIG. 3. Almost all of the examined monoclonal antibodies exhibited a neutralizing activity on strain SF162, which had been known to have high neutralization sensitivity. On the other hand, as to strains 89.6 and JR-FL, which were relatively resistant to neutralization, V3 antibodies {particularly, 0.5γ(IC10) and 5G2} exhibited a neutralizing activity, but CD4bs antibodies and CD4i antibodies exhibited only a weak neutralizing activity. Meanwhile, V3 antibodies were not effective for IIIB in which the amino acid sequence of V3-tip differed from those of other viruses, but some CD4bs and CD4i antibodies exhibited a neutralizing activity. These data suggest that cross-neutralizing activity on various HIV-1 strains in cases having the above-mentioned antibodies is mainly caused by the complementary neutralization between V3 antibodies and CD4bs antibodies. Among the aforementioned monoclonal antibodies, V3 antibodies, 0.5γ(IC10) and 5G2, and CD4bs antibodies, 0.5δ(3D6), 49G2 and 42F9, exhibited a strong neutralizing activity. A further neutralization experiment was carried out.

Example 6

Studies Regarding Neutralizing Activity on 17 Types of Viral Strains Including Clinically Isolated Strains Neutralizing activity on 17 types of viral strains including clinically isolated strains was studied (Table 2). For this neutralization experiment, the following MMT assay was applied. As a method, $2 \times 10^3$ PM1/CCR5 cells were infected with 100 TCID50 virus in the presence of the antibody in each concentration on a 96-well round-bottom micro culture plate, and the cells were then cultured at 37° C. for 7 days. Thereafter, 100 µl of a culture solution was removed from each well, and 10 µl of an MTT (3-[4,5-dimethylthiazol-2-yl]-2,5-diphenyltetrazolium bromide) solution dissolved in a phosphate-buffered saline (PBS) (7.5 mg/ml) was then added thereto. The obtained mixture was incubated at 37° C. for 3 hours. Thereafter, 100 µl of acidified isopropanol containing 4% Triton X-100 (vol/vol) was added to each well, so as to release formazan crystal. The absorbance (570 nm) was measured with a microplate reader, and the cell survival rate was calculated. This experiment was repeated 2 or 3 times. The antibody concentration necessary for inhibiting 50% virus infection ($IC_{50}$) was calculated, and the antibody concentration corresponding to such $IC_{50}$ was indicated with color-coding.

The neutralizing activities of antibodies on various HIV-1 strains including clinically isolated strains are shown in Table 2. The activity of clone 5G2 was equivalent to that of a KD-247 antibody as a related art. However, an anti-V3 antibody, 0.5γ(IC10), and CD4bs antibodies, 0.5δ(3D6) and 49G2, exhibited a wide range of strong neutralizing activity on HIV-1 of subtype B (Western type). It should be noted that strains, which were not neutralized by the anti-V3 antibody, 0.5γ(IC10), were neutralized by the CD4bs antibodies, 0.5δ (3D6) and 49G2. That is to say, a complementary neutralization was observed.

TABLE 2

Neutralizing activity of monoclonal antibodies on 17 types of viruses

| | | | anti-V3 mAbs | | | CD4 bs mAbs | | CD4i |
|---|---|---|---|---|---|---|---|---|
| | CoRc Usage | Subtype | KD247 | 5G2 | 1C10 | 3D6 | 9G2 | mAb 4C11 |
| laboratory strains (CXCR4-tropic virus) | | | | | | | | |
| IIIB | X4 | B | >50 | >50 | >50 | 2 | 1.6 | 26 |
| 89.6 | Dual | B | 4.2 | 14 | 0.12 | >50 | 5.8 | 15 |
| laboratory strains (CCR5-tropic virus) | | | | | | | | |
| SF162 | R5 | B | 0.21 | 0.91 | 0.053 | 2.3 | 2.5 | 27 |
| BaL | R5 | B | 3.8 | 5.8 | 0.25 | >50 | >50 | 37 |
| JRFLwt | R5 | B | 12 | 37 | 2.9 | >50 | 23 | >50 |

TABLE 2-continued

Neutralizing activity of monoclonal antibodies on 17 types of viruses

| | | | anti-V3 mAbs | | | CD4 bs mAbs | | CD4i |
|---|---|---|---|---|---|---|---|---|
| | CoRc Usage | Subtype | KD247 | 5G2 | 1C10 | 3D6 | 9G2 | mAb 4C11 |
| JRFLGPER | R5 | B | >50 | >50 | 26 | 1.2 | ND | ND |
| YU2 | R5 | B | >50 | >50 | 14 | >50 | >50 | >50 |
| | | | clinically isolated strains (Japan) | | | | | |
| MTA | R5 | B | 0.08 | 0.009 | 0.53 | 0.15 | 0.9 | 0.31 |
| MOKW | R5 | B | 0.11 | 0.012 | 0.02 | 0.42 | 2.2 | 19 |
| YKI | R5 | B | 0.5 | 1 | 0.01 | 2.4 | 1 | 0.1 |
| YIS | R5 | B | >50 | >50 | 0.59 | 2.3 | 1.8 | >50 |
| MIS | R5 | B | >50 | >50 | >50 | 0.15 | 0.25 | 18 |
| kKGO | R5 | B | >50 | >50 | 0.32 | >50 | 9.6 | >50 |
| KMT | X4 | B | >50 | >50 | 24 | 24 | >50 | >50 |
| | | | clinically isolated strains (Africa) | | | | | |
| TR43 | R5 | G | >50 | >50 | >50 | >50 | >50 | >50 |
| | | | HIV-2 strains | | | | | |
| ROD | X4 | HIV-2 | >50 | >50 | >50 | >50 | >50 | >50 |
| EHO | X4 | HIV-2 | >50 | >50 | >50 | >50 | >50 | >50 |

Example 7

Enhancement of Reactivity of V3 Antibodies by CD4bs Antibody 0.5δ

It has been known that gp120 undergose conformational changeafter it has bound to a CD4 molecule. On the other hand, almost no studies have been carried out regarding whether or not the CD4bs antibody induces such change in three-dimensional structure of gp120. The present inventors have considered the possibility that the CD4bs antibody causes a change in three-dimensional structure to gp120 after it has bound to the gp120, so as to change the reactivity of other antibodies. A "gp120-captured plate" was prepared by the above-mentioned gp120-capture ELISA method. Thereafter, 0.5δ(3D6) as a CD4bs antibody, or a control antibody (8D11), was allowed to react therewith at a concentration of 5 μg/ml for 15 minutes. Subsequently, biotin (Pierce, Rockford Ill.)-bound antibodies, 1C10, 3E4, 3D6, and 4C11, were allowed to react therewith at each concentration for 2 hours. Thereafter, the resultant was washed with an ELISA wash buffer, it was then allowed to react with avidin-ALP (Zymed) for 1 hour, and a substrate was then added thereto for color development. The results are shown in FIG. 4. The reactivity of biotinylated V3 antibodies, 0.5γ(1C10) and 3E4, with gp120 was significantly enhanced in the presence of 0.5δ. On the other hand, the reactivity of biotinylated antibodies, 0.5δ (3D6) and 4C11, was suppressed in the presence of 0.5δ. Thus, it was found that the CD4bs antibody, 0.5δ, causes a change in three-dimensional structure to gp120 by itself, and that it drastically expands the reactivity of V3 antibodies (particularly 0.5γ).

Example 8

Synergistic Neutralizing Effect by the Combined Use of 0.5δ and 0.5γ

As described above, 0.5δ enhances the reactivity of 0.5γ. Hence, the combination effect of 0.5δ and 0.5γ was studied regarding neutralizing activity. By combining 0.5δ and 0.5γ in various concentrations, their neutralizing activity on a JR-FL strain was analyzed by an MTT assay. As shown in FIG. 5, as a result of the combined use of the two antibodies, the synergistic enhancement of neutralizing activity was observed. In order to analyze such synergistic effect, the analysis method of Chow/Talaley et al. and the 3-dimensional analysis method were applied. As a result of the in vitro observation of such antibodies, it was assumed that a stronger neutralization reaction might occur as a result of the interaction of the V3 antibody with the CD4bs antibody in vivo. Based on these data, it was considered that both the V3 antibody and the CD4bs antibody that react with a wide range of strains are necessary for a wide and strong neutralizing antibody reaction.

Example 9

Neutralizing Activity on International Standard Virus Panels

In order to evaluate data regarding AIDS vaccine development on an international basis, viruses serving as standards are furnished from an institute in the United States (NIAID ARRP). Neutralization data obtained using the panels of subtype (clade) B viruses (Standard Virus Panels B; SVPB) consisting of 12 types of pseudotyped viruses are shown in Table 3. As shown in Table 3, 0.5γ(IC10) was able to suppress 50% or more of the growth of 7/12 viruses at a concentration of 50 μg/ml, and it was also able to suppress 50% or more of the growth of 10/12 viruses at a concentration of 150 μg/ml. On the other hand, with regard to the results of the antibodies of related art, b12 suppressed 50% or more of the growth of 8/12 viruses, 2G12 suppressed 50% or more of the growth of 6/12 viruses, and 447-52D suppressed 50% or more of the growth of 3/12 viruses. The data of the b12, 2G12 and 447-52D (447D) as related art antibodies were cited from a study paper (Li M. et. al, J. Virol. 79, pp. 10108-10125, 2005). The data of b12 and 2G12 only exist up to a concentration of 50 μg/ml, and the data of 447-52D(447D) only exist up to a concentration of 25 μg/ml. Thus, these related art antibodies cannot be necessarily used for a simple comparison. However, apparently differing from these related art antibodies, 0.5γ(IC10) is found to exhibit a wide neutralizing activity. Also, b12 as a CD4bs antibody has a wide range of neutralizing activity, but this is a special antibody having a long, heavy chain CDR3 consisting of 18 amino acids, which is often observed in autoantibodies (Saphire E O. et al., Science 239, pp. 1155-1159). On the other hand, 0.5γ(IC10) has CDR3 consisting of 11 amino acids.

SEQ ID NO: 15 Nucleotide sequence of the H chain variable region (VH) of 0.5δ (3D6)
SEQ ID NO: 16 Nucleotide sequence of the L chain variable region (VL) of 0.5δ (3D6)

TABLE 3

Neutralizing activity of monoclonal antibodies on Standard viral panel B ($IC_{50}$)

| standard panel | IC50 in TZM-bl cells(μg/ml) | | | | | | | | | | | | |
|---|---|---|---|---|---|---|---|---|---|---|---|---|---|
| pseudo virus | 1C10 | 1C10 | 3D6 | 9G2 | 2F9 | 3E4 | 5G2 | 2F8 | KD247 | 8D11 | IgGb12* | 2G12* | 447D* |
| SVPB5 | 0.23 | | 1.2 | 2.1 | 4.5 | >50 | 10.1 | >50 | 1.8 | >50 | 1.4 | 2 | 0.1 |
| SVPB6 | 38 | | >50 | >50 | >50 | >50 | >50 | >50 | >50 | >50 | 0.3 | 2.8 | >25 |
| SVPB8 | >50 | >150 | >50 | >50 | >50 | >50 | >50 | >50 | >50 | >50 | 0.2 | 2.1 | >25 |
| SVPB11 | 35 | | >50 | >50 | >50 | >50 | >50 | >50 | >50 | >50 | >50 | 1.2 | >25 |
| SVPB12 | >50 | 82 | >50 | 7.8 | >50 | — | >50 | >50 | >50 | >50 | >50 | 0.4 | >25 |
| SVPB13 | >50 | 110 | >50 | >50 | >50 | — | >50 | >50 | >50 | >50 | 1.9 | >50 | >25 |
| SVPB14 | 10.5 | | >50 | >50 | >50 | >50 | >50 | >50 | >50 | >50 | 0.1 | >50 | >25 |
| SVPB15 | >50 | >150 | >50 | >50 | >50 | >50 | >50 | >50 | >50 | >50 | 0.5 | >50 | >25 |
| SVPB16 | 6.1 | | >50 | 7.8 | 21 | >50 | >50 | >50 | >50 | >50 | 0.7 | >50 | >25 |
| SVPB17 | 4.5 | | >50 | >50 | >50 | >50 | 50 | >50 | 17 | >50 | >50 | >50 | >25 |
| SVPB18 | 1.1 | | >50 | >50 | >50 | >50 | 11.5 | >50 | 28 | >50 | 3.1 | 1.1 | >25 |

*The data were taken from Li, M. et al., *J. Virol.* 79.16.10108-10125, 2005)

Example 10

Figure 12:
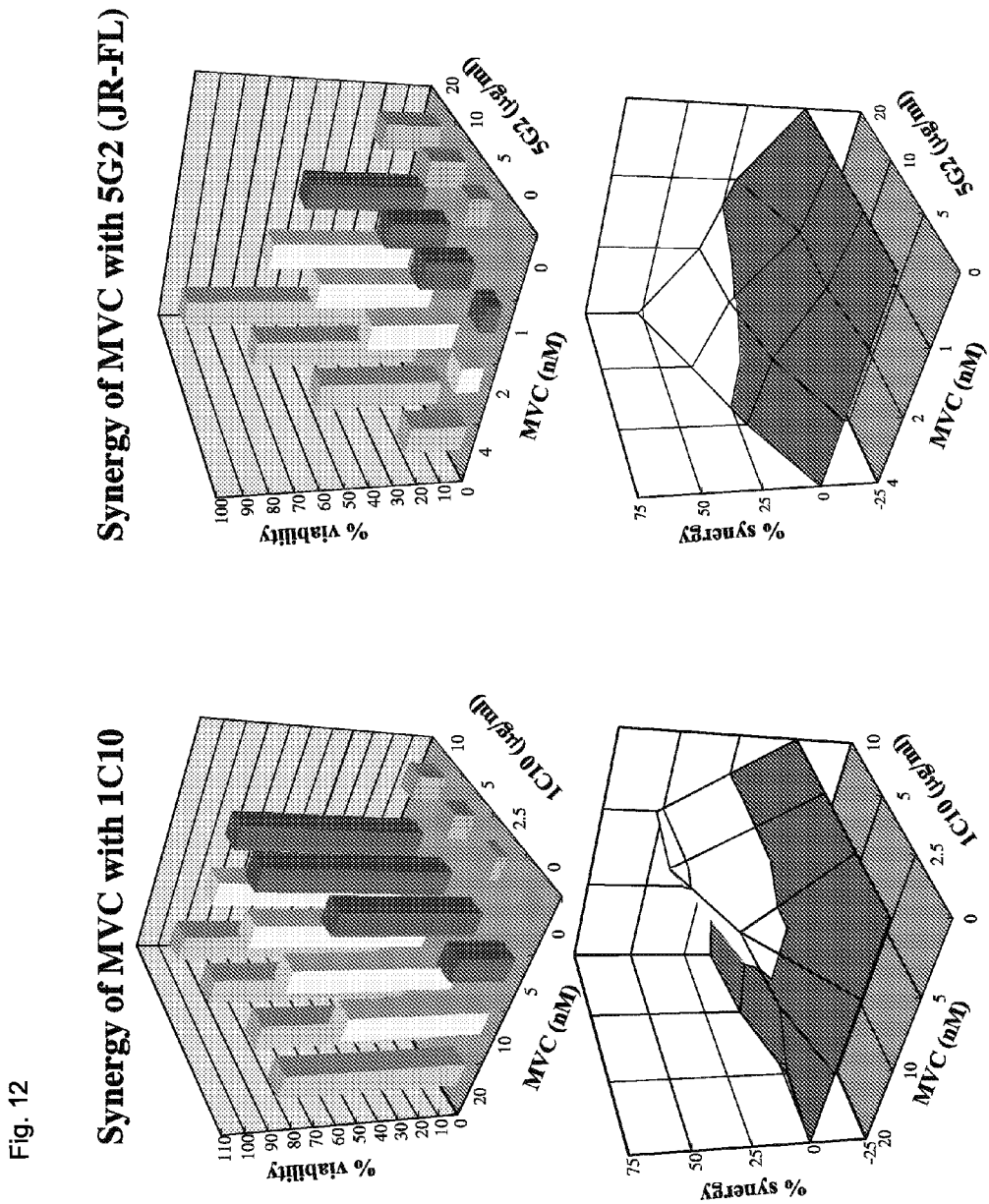
FIG. 12 shows the synergistic inhibitory effect obtained by the combined use of a CCR5 inhibitor with the antibody of the present invention.

Determination of Gene Sequence of Antigen-Antibody Binding Site of Monoclonal Antibody The present inventors have determined the gene sequences of the antigen-binding sites of representative neutralizing monoclonal antibodies (anti-V3: 0.5γ(IC10) and 5G2; CD4bs: 0.5δ(3D6), 42F9, 49G2). The results are shown in FIGS. 6 to 10, and SEQ ID NOS: 1 to 20 in the sequence listing. As a method, RNA was extracted from each cell line, and VH and VL were amplified by PCR and were then identified according to the method of Marks et al. (Marks, J. D. et. al., J. Mol. Biol., 222: 581-597, 1991).
SEQ ID NO: 1 Amino acid sequence of the H chain variable region (VH) of 0.5γ(1C10)
SEQ ID NO: 2 Amino acid sequence of the L chain variable region (VL) of 0.5γ(1C10)
SEQ ID NO: 3 Amino acid sequence of the H chain variable region (VH) of 5G2
SEQ ID NO: 4 Amino acid sequence of the L chain variable region (VL) of 5G2
SEQ ID NO: 5 Amino acid sequence of the H chain variable region (VH) of 0.5δ (3D6)
SEQ ID NO: 6 Amino acid sequence of the L chain variable region (VL) of 0.5δ (3D6)
SEQ ID NO: 7 Amino acid sequence of the H chain variable region (VH) of 42F9
SEQ ID NO: 8 Amino acid sequence of the L chain variable region (VL) of 42F9
SEQ ID NO: 9 Amino acid sequence of the H chain variable region (VH) of 49G2
SEQ ID NO: 10 Amino acid sequence of the L chain variable region (VL) of 49G2
SEQ ID NO: 11 Nucleotide sequence of the H chain variable region (VH) of 0.5γ(1C10)
SEQ ID NO: 12 Nucleotide sequence of the L chain variable region (VL) of 0.5γ(1C10)
SEQ ID NO: 13 Nucleotide sequence of the H chain variable region (VH) of 5G2
SEQ ID NO: 14 Nucleotide sequence of the L chain variable region (VL) of 5G2
SEQ ID NO: 17 Nucleotide sequence of the H chain variable region (VH) of 42F9
SEQ ID NO: 18 Nucleotide sequence of the L chain variable region (VL) of 42F9
SEQ ID NO: 19 Nucleotide sequence of the H chain variable region (VH) of 49G2
SEQ ID NO: 20 Nucleotide sequence of the L chain variable region (VL) of 49G2
(Discussion)

These new monoclonal antibodies all exhibited a wide range of strong neutralizing activity on subtype (clade) B viruses. In particular, 0.5γ(IC10) is considered to be the highest level of antibody that can be currently used. These antibodies do not only play an important role in the development of vaccine, but the antibodies, the fragments thereof, or molecules produced based on the genes thereof can also be used for the prevention and/or treatment of AIDS/HIV infection.

Example 11

Studies Regarding Neutralizing Activity on Various Types of Viral Strains

As with the panels of subtype (clade) B viruses (SVPB), the panels of subtype C viruses have also been supplied. As shown in FIG. 11, when compared with a control antibody, the CD4bs antibodies, 0.5δ(3D6), 49G2 and 42F9, exhibited a clear neutralizing activity on two viruses (SVPC13 and SVPC15) among the subtype C virus panels. In addition, these CD4bs antibodies exhibited a neutralizing activity also on subtype AE viruses, 93TH976.17 and 93TH966.8. The three above CD4bs antibodies exhibited a neutralizing activity on viruses other than subtype B viruses. Thus, it is considered that they are important for the studies of cross-clade neutralization by antibodies.

The results are shown in FIG. 11. The antibodies of the present invention, 0.5δ(3D6), 49G2 and 42F9, exhibited an inhibitory activity on the examined SVPC13, SVPC15, 93TH976.17, and 93TH966.8.

Example 12

Combined Use of CCR5 Inhibitor with Antibody of the Present Invention

After gp120 has bound to CD4, V3 binds to a coreceptor (CCR5 or CXCR4), so that the virus invades the cell. V3 serving as an epitope of 0.5γ or 5G2 and a CCR5 inhibitor (maraviroc, MVC) serving as a counterpart of binding therewith are considered to be an important combination even from the viewpoint of clinical application. Hence, the neutralizing activity of the combination of the V3 antibody with the CCR5 inhibitor (MVC) on the JR-FL strain was examined by an MTT assay. As shown in FIG. 12, it was observed that the synergistic enhancement of the neutralizing activity was obtained by the combined use of the V3 antibody with MVC. For the analysis of such synergistic effect, a 3-dimensional analysis method was applied. As a result of such in vitro observation, it is assumed that the V3 antibody interacts with the CCR5 inhibitor, so as to cause a stronger virus-suppressing effect. Based on these data, it is considered that the combined use of the V3 antibody with the CCR5 inhibitor may enhance therapeutic effects, when they are clinically administered.

The results are shown in FIG. 12. By the combined use of the antibody of the present invention, 0.5γ(1C10) or 5G2, with the CCR5 inhibitor, a synergistic inhibitory effect on HIV-1JRFL was observed.

INDUSTRIAL APPLICABILITY

The current treatment of HIV infection (namely, a multi-drug therapy using antiviral agents; HAART (highly active antiretroviral therapy)) is able to suppress the growth of virus, but is not able to completely cure the disease. Once the treatment has started, the patient should continue the HAART. Since antiviral agents are chemical substances, various long-term toxicities appear in the continued treatment over a long period of time, and thereby, patients are forced to terminate the treatment in many cases. In contrast, the antibody of the present invention is able to become a mainstream of a new therapy (combination therapy) having no side effects. In addition, the antibody of the present invention can also be used as an antiserum in a needle-stick accident, and it can be further used as a reagent necessary for the development of effective vaccine.

The invention claimed is:

1. A monoclonal antibody that binds specifically to an epitope present in the V3 loop of the envelope glycoprotein gp120 of the AIDS virus, which is any one selected from the following antibodies:
   (a) an antibody having the amino acid sequence shown in SEQ ID NO: 1 as the amino acid sequence of a H chain variable region (VH), and having the amino acid sequence shown in SEQ ID NO: 2 as the amino acid sequence of a L chain variable region (VL); and
   (b) an antibody having the amino acid sequence shown in SEQ ID NO: 3 as the amino acid sequence of a H chain variable region (VH), and having the amino acid sequence shown in SEQ ID NO: 4 as the amino acid sequence of a L chain variable region (VL).

2. A monoclonal antibody that binds specifically to an epitope present in the V3 loop of the envelope glycoprotein gp120 of the AIDS virus, which is produced by an isolated immortalized cell line having accession No. FERM BP-11021 or accession No. FERM BP-11060, or a fragment thereof which is selected from F(ab')₂ or Fab'.

3. The antibody according to claim 1, which is produced by cells that are obtained by screening the B cells of HIV-infected patients in long-term nonprogressive HIV infection cases, in terms of binding ability to gp120, and then selecting B cells that produce gp120-binding antibodies.

4. A method for producing the antibody of claim 1, which comprises culturing an isolated immortalized cell line having accession No. FERM BP-11021 or accession No. FERM BP-11060, and collecting the antibody produced by the isolated immortalized cell line having accession No. FERM BP-11021 or accession No. FERM BP-11060.

5. An isolated immortalized cell line which produces the antibody of claim 1, having accession No. FERM BP-11021 or accession No. FERM BP-11060.

6. A pharmaceutical composition comprising the antibody of claim 1 and a pharmaceutically acceptable carrier.

7. A pharmaceutical composition comprising the combination of
   the monoclonal antibody of claim 1 and
   a monoclonal antibody that recognizes the CD4-binding site of the envelope glycoprotein gp120 of the AIDS virus, which is any one selected from the following antibodies:
   (a) an antibody having the amino acid sequence shown in SEQ ID NO: 5 as the amino acid sequence of a H chain variable region (VH), and having the amino acid sequence shown in SEQ ID NO: 6 as the amino acid sequence of a L chain variable region (VL);
   (b) an antibody having the amino acid sequence shown in SEQ ID NO: 7 as the amino acid sequence of a H chain variable region (VH), and having the amino acid sequence shown in SEQ ID NO: 8 as the amino acid sequence of a L chain variable region (VL); and
   (c) an antibody having the amino acid sequence shown in SEQ ID NO: 9 as the amino acid sequence of a H chain variable region (VH), and having the amino acid sequence shown in SEQ ID NO: 10 as the amino acid sequence of a L chain variable region (VL).

* * * * *

SEQUENCE LISTING

```
<160> NUMBER OF SEQ ID NOS: 21

<210> SEQ ID NO 1
<211> LENGTH: 119
<212> TYPE: PRT
<213> ORGANISM: Homo sapiens

<400> SEQUENCE: 1

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Ser
            20                  25                  30

Ser Met Ser Trp Val Arg Gln Ala Pro Glu Lys Gly Leu Glu Trp Val
        35                  40                  45

Ser Val Val Tyr Ser Gly Gly Asn Thr Tyr Asn Ala Asp Ser Val Lys
    50                  55                  60

Gly Arg Phe Ser Ile Ser Arg Asp Asn Ser Lys Asn Thr Val Tyr Leu
65                  70                  75                  80

Gln Met Asn Ser Leu Arg Ala Asp Thr Ala Val Tyr Tyr Cys Ala
            85                  90                  95

Arg Asp Leu Gly Gly Gly Asp Arg Ser Ser Asp Tyr Trp Gly Gln Gly
                100                 105                 110

Thr Leu Val Thr Val Ser Ser
        115

<210> SEQ ID NO 2
<211> LENGTH: 109
<212> TYPE: PRT
<213> ORGANISM: Homo sapiens

<400> SEQUENCE: 2

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Ile Asn Thr Tyr
            20                  25                  30

Leu Asn Trp Tyr Gln Gln Arg Pro Gly Lys Ala Pro Lys Leu Leu Ile
        35                  40                  45

Tyr Ala Ala Ser Thr Leu Gln Thr Gly Val Pro Ser Arg Phe Ser Gly
    50                  55                  60
```

```
Ser Gly Ser Gly Thr Leu Phe Thr Leu Thr Ile Ser Ser Leu Gln Pro
 65                  70                  75                  80

Glu Asp Leu Ala Thr Tyr Tyr Cys Gln Gln Ser Phe Ser Thr Leu Pro
                 85                  90                  95

Tyr Thr Leu Gly Arg Gly Thr Lys Val Glu Ile Lys Gly
            100                 105
```

<210> SEQ ID NO 3
<211> LENGTH: 123
<212> TYPE: PRT
<213> ORGANISM: Homo sapiens

<400> SEQUENCE: 3

```
Glu Val Gln Leu Val Glu Ser Gly Gly Val Val Arg Pro Gly Asn
 1               5                  10                  15

Ser Leu Arg Leu Ser Cys Ala Ala Ser Gly Ile Ile Phe Ser Thr Ala
                 20                  25                  30

Asn Leu His Trp Leu Arg His Val Pro Gly Lys Gly Leu Glu Trp Val
             35                  40                  45

Ala Ile Ile Ser Tyr Asp Gly His Arg Gln Tyr Tyr Ala Asp Leu Val
 50                  55                  60

Lys Gly Arg Phe Thr Ile Ser Arg Asp Asn Ser Lys Asn Thr Leu His
 65                  70                  75                  80

Leu Gln Met Asp Gly Leu Thr Ser Asp Thr Ala Val Tyr Tyr Cys
                 85                  90                  95

Ala Lys Asp Gly Ala Asp Glu Asn Asn Leu Gly Pro Ala Phe Asp Tyr
            100                 105                 110

Trp Gly Arg Gly Thr Leu Val Thr Val Ser Ser
            115                 120
```

<210> SEQ ID NO 4
<211> LENGTH: 108
<212> TYPE: PRT
<213> ORGANISM: Homo sapiens

<400> SEQUENCE: 4

```
Glu Ile Val Leu Thr Gln Ser Pro Ala Thr Leu Ser Val Ser Pro Gly
 1               5                  10                  15

Glu Gly Ala Thr Leu Ser Cys Arg Ala Ser Gln Ser Ile Ser Ser Asn
                 20                  25                  30

Leu Ala Trp Tyr Gln Gln Lys Pro Gly Gln Ala Pro Arg Leu Leu Ile
             35                  40                  45

Tyr Gly Ala Ser Thr Gly Ala Thr Gly Ile Pro Ala Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Ile Tyr Tyr Cys Gln Gln Tyr Gly Ser Leu Pro Ile
                 85                  90                  95

Thr Phe Gly Gln Gly Thr Arg Leu Glu Ile Lys Arg
            100                 105
```

<210> SEQ ID NO 5
<211> LENGTH: 129
<212> TYPE: PRT
<213> ORGANISM: Homo sapiens

<400> SEQUENCE: 5

```
Glu Val Gln Leu Val Glu Ser Ala Ala Glu Val Lys Lys Pro Gly Ala
```

```
                1               5                   10                  15
            Ser Val Lys Val Ser Cys Lys Ala Ser Gly Tyr Thr Phe Thr Ser Tyr
                            20                  25                  30

Gly Ile Ser Trp Val Arg Gln Ala Pro Gly Gln Gly Leu Gln Trp Met
                            35                  40                  45

Gly Trp Ile Ser Ala Tyr Asn Gly Asn Thr Lys Phe Ala Gln Glu Phe
                50                          55                  60

Lys Gly Arg Val Thr Met Thr Thr Asp Thr Ser Ala Thr Thr Ala Tyr
             65                         70                  75                  80

Met Glu Leu Arg Ser Leu Arg Ser Asp Thr Ala Val Tyr Tyr Cys
                            85                  90                  95

Ala Arg Arg Asn Tyr Tyr Asp Ser Gly Ser Tyr Tyr Ile Arg Asp Gly
                            100                 105                 110

Asp Tyr Ser Met Asp Val Trp Gly Gln Gly Thr Leu Val Thr Val Ser
                            115                 120                 125

Ser

<210> SEQ ID NO 6
            <211> LENGTH: 111
            <212> TYPE: PRT
            <213> ORGANISM: Homo sapiens

<400> SEQUENCE: 6

Gln Ser Val Leu Thr Gln Pro Pro Ser Ala Ser Gly Thr Pro Gly Gln
             1               5                   10                  15

Arg Val Thr Ile Ser Cys Ser Gly Ser Gly Ser Asn Ile Gly Ser Asn
                            20                  25                  30

Thr Val Asn Trp Tyr Gln Gln Phe Pro Gly Thr Ala Pro Lys Leu Leu
                            35                  40                  45

Ile Tyr Asn Asn Asn Gln Arg Pro Ser Gly Val Pro Asp Arg Phe Ser
                50                          55                  60

Gly Ser Lys Ser Gly Thr Ser Ala Ser Leu Ala Ile Ser Gly Leu Gln
             65                         70                  75                  80

Ser Ala Asp Glu Ala Asp Tyr Tyr Cys Ala Thr Trp Asp Asp Ser Leu
                            85                  90                  95

Asp Gly Trp Val Phe Gly Gly Gly Thr Lys Leu Thr Val Leu Gly
                            100                 105                 110

<210> SEQ ID NO 7
            <211> LENGTH: 126
            <212> TYPE: PRT
            <213> ORGANISM: Homo sapiens

<400> SEQUENCE: 7

Glu Val Gln Leu Val Glu Ser Gly Gly Gly Val Val Arg Pro Gly Gly
             1               5                   10                  15

Ser Leu Arg Leu Ser Cys Ala Ala Ser Gly Phe Ala Phe Gly Glu Tyr
                            20                  25                  30

Gly Met Ser Trp Val Arg Gln Ala Pro Gly Lys Gly Leu Glu Trp Val
                            35                  40                  45

Ser Gly Ile Asn Trp Asn Gly Gly Ser Thr Gly Tyr Ala Asp Ser Val
                50                          55                  60

Gln Gly Arg Phe Thr Thr Ser Arg Asp Asn Ala Lys Asn Ser Leu Tyr
             65                         70                  75                  80

Leu Gln Met Asn Ser Leu Arg Ala Glu Asp Thr Ala Leu Tyr Tyr Cys
                            85                  90                  95
```

```
Ala Arg Asp Glu Asn Tyr Asp Ile Leu Thr Gly Asn Tyr Tyr Tyr Gly
            100                 105                 110

Met Asp Val Trp Gly Gln Gly Thr Thr Val Thr Val Ser Ser
        115                 120                 125

<210> SEQ ID NO 8
<211> LENGTH: 108
<212> TYPE: PRT
<213> ORGANISM: Homo sapiens

<400> SEQUENCE: 8

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Phe Tyr Cys Gln Gln Ser His Ser Ile Pro Tyr
                85                  90                  95

Thr Phe Gly Gln Gly Thr Lys Leu Glu Ile Lys Arg
            100                 105

<210> SEQ ID NO 9
<211> LENGTH: 121
<212> TYPE: PRT
<213> ORGANISM: Homo sapiens

<400> SEQUENCE: 9

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Pro Ile Ala Ala Ala Thr His Ala Phe Asp Ile Trp Gly
            100                 105                 110

Gln Gly Thr Met Val Thr Val Ser Ser
        115                 120

<210> SEQ ID NO 10
<211> LENGTH: 111
<212> TYPE: PRT
<213> ORGANISM: Homo sapiens

<400> SEQUENCE: 10

Gln Ser Val Leu Thr Gln Pro Pro Ser Ala Ser Gly Thr Pro Gly Gln
1               5                   10                  15

Arg Val Thr Ile Ser Cys Ser Gly Ser Gly Ser Asn Ile Gly Ser Asn
            20                  25                  30
```

```
Thr Val Asn Trp Tyr Gln Gln Phe Pro Gly Thr Ala Pro Lys Leu Leu
         35                  40                  45

Ile Tyr Asn Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Ala Asp Glu Ala Asp Tyr Tyr Cys Ala Thr Trp Asp Asp Ser Leu
                 85                  90                  95

Asp Gly Trp Val Phe Gly Gly Gly Thr Lys Leu Thr Val Leu Gly
             100                 105                 110
```

<210> SEQ ID NO 11
<211> LENGTH: 357
<212> TYPE: DNA
<213> ORGANISM: Homo sapiens

<400> SEQUENCE: 11

```
gaggtgcagc tggtggagtc tgaggaggt ttgatccagc ctggggggtc cctgagactc    60
tcctgtgcag cctctgggtt cacagtcagt agcagcagca tgagctgggt ccgccaggct   120
ccagagaagg ggctggagtg ggtctcagtt gtttatagcg gtgggaacac atataacgca   180
gactccgtga agggccgatt cagcatctcc agagacaatt ccaagaacac ggtatatctt   240
cagatgaaca gcctgagagc cgacgacacg gccgtgtatt actgtgcgag agatttaggg   300
ggggggacc ggtcctctga ctactgggc cagggcaccc tggtcaccgt ctcctca      357
```

<210> SEQ ID NO 12
<211> LENGTH: 327
<212> TYPE: DNA
<213> ORGANISM: Homo sapiens

<400> SEQUENCE: 12

```
gacatccagt tgacccagtc tccatcctcc ctgtctgcat ctgtgggaga cagagtcacc    60
atcacttgcc gggcaagtga gagcattaac acctatttaa attggtatca acagagacca   120
gggaaagccc ctaaactcct gatctatgct gcatccactt tacaaactgg ggtcccatca   180
aggttcagtg gcagtgggtc tgggacactt ttcactctca ccatcagcag tctgcaacct   240
gaggatcttg caacttatta ctgtcaacag agtttcagta ccctcccgta cactcttggc   300
cgggggacca aggtggagat caaaggt                                         327
```

<210> SEQ ID NO 13
<211> LENGTH: 369
<212> TYPE: DNA
<213> ORGANISM: Homo sapiens

<400> SEQUENCE: 13

```
gaggtgcagc tggtggagtc tgggggaggc gtggtccggc ctgggaactc cctgagactc    60
tcctgtgcag cctctggaat catcttcagt accgctaatt tacactggct ccgccacgtt   120
ccaggcaagg gcctggagtg ggtggccatt atttcatatg atggccacag acaatactac   180
gcagacctcg tgaagggccg attcaccatc tccagagaca attccaagaa caccctgcat   240
ctgcaaatgg acggcctgac atctgacgac acggctgtct attattgtgc gaaagacggg   300
gcagatgaga acaatttagg tccgcctttt gactactggg gccggggcac cctggtcacc   360
gtctcctca                                                             369
```

<210> SEQ ID NO 14

<210> SEQ ID NO 14
<211> LENGTH: 324
<212> TYPE: DNA
<213> ORGANISM: Homo sapiens

<400> SEQUENCE: 14

| | | | | | | |
|---|---|---|---|---|---|---|
| gaaattgtgt | tgacgcagtc | tccagccacc | ctgtctgtat | caccagggga | aggagccacc | 60 |
| ctctcctgca | gggccagtca | gagtattagc | agcaacttag | cctggtacca | gcagaagcct | 120 |
| ggccaggctc | ccaggctcct | catctatggt | gcatccaccg | gggccactgg | tatcccagcc | 180 |
| aggttcagtg | gcagtgggtc | tgggacagac | ttcactctca | ccatcagcag | actggagcct | 240 |
| gaagattttg | cgatttatta | ctgtcagcag | tatggtagtt | taccgataac | cttcggccaa | 300 |
| gggacacgac | tggagattaa | acgt | | | | 324 |

<210> SEQ ID NO 15
<211> LENGTH: 387
<212> TYPE: DNA
<213> ORGANISM: Homo sapiens

<400> SEQUENCE: 15

| | | | | | | |
|---|---|---|---|---|---|---|
| gaggtgcagc | tggtggagtc | tgcagctgag | gtgaagaagc | ctggggcctc | agtgaaggtc | 60 |
| tcctgcaagg | cttctggtta | cacttttacc | agctatggta | tcagctgggt | gcgacaggcc | 120 |
| cctggacaag | gcttcagtg | atgggatgg | atcagcgctt | acaacggtaa | cactaagttt | 180 |
| gcacaagaat | ttaagggcag | agtcaccatg | accacagaca | catccgcgac | acagcctac | 240 |
| atggagctga | ggagcctgag | atctgacgac | acggccgtgt | attattgtgc | gaggaggaat | 300 |
| tactatgatt | cggggagtta | ttatattcgt | gacggggact | acagtatgga | tgtctggggc | 360 |
| caaggcaccc | tggtcaccgt | ctcctca | | | | 387 |

<210> SEQ ID NO 16
<211> LENGTH: 333
<212> TYPE: DNA
<213> ORGANISM: Homo sapiens

<400> SEQUENCE: 16

| | | | | | | |
|---|---|---|---|---|---|---|
| cagtctgtgc | tgactcagcc | gccctcagcg | tctgggaccc | ccgggcagag | ggtcaccatc | 60 |
| tcttgttctg | gaagcggctc | caacatcgga | agtaatactg | taaactggta | ccagcagttc | 120 |
| ccaggaacgg | cccccaaact | cctcatctat | aataataatc | agcggccctc | agggtccct | 180 |
| gaccgattct | ctggctccaa | gtctggcacc | tcagcctccc | tggccatcag | tgggctccag | 240 |
| tctgcggatg | aggctgatta | ttactgtgca | acatgggatg | acagcctgga | tggttgggtg | 300 |
| ttcggcggag | ggaccaagct | gaccgtccta | ggt | | | 333 |

<210> SEQ ID NO 17
<211> LENGTH: 377
<212> TYPE: DNA
<213> ORGANISM: Homo sapiens

<400> SEQUENCE: 17

| | | | | | | |
|---|---|---|---|---|---|---|
| gaggtgcagc | tggtggagtc | tgggggaggt | gtggtacggc | ctgggggtc | cctgagactc | 60 |
| tcctgtgcag | cctctggatt | cgcctttggt | gagtatggca | tgagctgggt | ccgccaagct | 120 |

```
ccagggaagg ggctggagtg ggtctctggt attaattgga atggtggtag cacaggttat      180
gcagactctg tgcagggccg attcaccacc tccagagaca acgccaagaa ctccctgtat      240
ctgcaaatga acagtctgag agccgaggac acggccttgt attactgtgc gagagatgag      300
aattacgata ttttgactgg taactactac tacggtatgg acgtctgggg ccaagggacc      360
acggtcaccg tctcctc                                                    377

<210> SEQ ID NO 18
<211> LENGTH: 324
<212> TYPE: DNA
<213> ORGANISM: Homo sapiens

<400> SEQUENCE: 18
gacatccagt tgacccagtc tccatcctcc ctgtctgcat ctgtgggaga cagagtcacc       60
atcacttgcc gggcaagtca gagcattagc aactatttaa attggtatca gcagaaacca      120
gggaaagccc ctaagctcct gatctatgct gcatccagtt tgcaaagtgg ggtcccatca      180
aggtttagtg gcagtggatc tgggacagat ttcactctca ccatcagcag tctgcaacct      240
gaagattttg caactttcta ctgtcaacag agtcacagta tccctacac ttttggccag       300 gggaccaagc tggagatcaa acgt                                             324

<210> SEQ ID NO 19
<211> LENGTH: 363
<212> TYPE: DNA
<213> ORGANISM: Homo sapiens

<400> SEQUENCE: 19
gaggtgcagc tggtgcagtc tggggctgag gtgaagaagc ctggggcctc agtgaaggtc       60
tcctgcaagg cttctggata caccttcacc ggctactata tgcactgggt gcgacaggcc      120
cctggacaag gcttgagtg gatgggatgg atcaaccctaa acagtggtgg cacaaactat      180
gcacagaagt ttcagggcag ggtcaccatg accagggaca cgtccatcag cacagcctac      240
atggagctga gcaggctgag atctgacgac acggccgtgt attactgtgc gagaggacct      300
atagcagcag caacccatgc ttttgatatc tggggccaag gacaatggt caccgtctct       360 tca                                                                    363

<210> SEQ ID NO 20
<211> LENGTH: 333
<212> TYPE: DNA
<213> ORGANISM: Homo sapiens

<400> SEQUENCE: 20
cagtctgtgc tgactcagcc accctcagcg tctgggaccc ccgggcagag ggtcaccatc       60
tcttgttctg gaagcggctc caacatcgga agtaatactg taaactggta ccagcagttc      120
ccaggaacgg cccccaaact cctcatctat aataataatc agcggccctc aggggtccct      180
gaccgattct ctggctccaa gtctggcacc tcagcctccc tggccatcag tgggctccag      240
tctgcggatg aggctgatta ttactgtgca acatgggatg acagcctgga tggttgggtg      300
ttcggcggag ggaccaagct gaccgtccta ggt                                   333
```

-continued

```
<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asn Asn Thr Arg Ile Ser Ile His Ile Gly Pro Gly Arg Ala Phe Val
1               5                   10                  15

Thr Ile Gly Lys
            20
```